(12) United States Patent
Chang et al.

(10) Patent No.: US 11,660,380 B2
(45) Date of Patent: *May 30, 2023

(54) BREAST PUMP SYSTEM WITH COLLECTION CONTAINER

(71) Applicant: Willow Innovations, Inc., Mountain View, CA (US)

(72) Inventors: John Chang, Los Altos, CA (US); Joshua Makower, Los Altos Hills, CA (US); Brian Mason, Lexington, MA (US); Fred Co, Santa Clara, CA (US); Mathew Calmer, Sacramento, CA (US); Arash Sabet, Walnut Creek, CA (US)

(73) Assignee: Willow Innovations, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/082,776

(22) Filed: Dec. 16, 2022

(65) Prior Publication Data

US 2023/0123294 A1    Apr. 20, 2023

Related U.S. Application Data

(63) Continuation of application No. 16/050,201, filed on Jul. 31, 2018, which is a continuation of application
(Continued)

(51) Int. Cl.
*A61M 1/06* (2006.01)
*A61M 1/00* (2006.01)

(52) U.S. Cl.
CPC .............. *A61M 1/06* (2013.01); *A61M 1/064* (2014.02); *A61M 1/067* (2021.05);
(Continued)

(58) Field of Classification Search
CPC ........ A61M 1/06; A61M 1/062; A61M 1/064; A61M 1/066; A61M 1/068; A61M 1/067;
(Continued)

(56) References Cited

U.S. PATENT DOCUMENTS 1,197,011 A    9/1916 Cilino
4,263,912 A    4/1981 Adams
(Continued)

FOREIGN PATENT DOCUMENTS

CN    2628060 Y    7/2004
CN    201692384    1/2011
(Continued)

OTHER PUBLICATIONS

Chiu et a., Development of a piezoelectric polyvinyildene fluoride (PVDF) polymer based sensor patch for simultaneous heartbeat and respiration monitoring, Sensors and Actuators A: Physical, vol. 189, Jan. 15, 2013, pp. 328-334.
(Continued)

*Primary Examiner* — Nathan R Price
*Assistant Examiner* — Anh Bui

(57) ABSTRACT

Systems and methods for pumping milk from a breast, wherein the milk is expressed from the breast under suction and milk is expulsed from the pumping mechanism to a collection container under positive pressure.

9 Claims, 24 Drawing Sheets

Related U.S. Application Data

No. PCT/US2017/017112, filed on Feb. 9, 2017, application No. 16/934,380, filed on Jul. 21, 2020 is a continuation of application No. 16/667,749, filed on Oct. 29, 2019, now Pat. No. 10,722,624, which is a continuation of application No. 15/180,345, filed on Jun. 13, 2016, now Pat. No. 10,688,229, which is a continuation of application No. PCT/US2015/041257, filed on Jul. 21, 2015.

(60) Provisional application No. 62/450,528, filed on Jan. 25, 2017, provisional application No. 62/442,008, filed on Jan. 4, 2017, provisional application No. 62/421,263, filed on Nov. 12, 2016, provisional application No. 62/293,480, filed on Feb. 10, 2016, provisional application No. 62/027,685, filed on Jul. 22, 2014.

(52) U.S. Cl.
CPC ...... *A61M 1/0697* (2021.05); *A61M 1/06935* (2021.05); *A61M 1/60* (2021.05); *A61M 1/74* (2021.05); *A61M 1/80* (2021.05); *A61M 2205/27* (2013.01); *A61M 2205/3331* (2013.01); *A61M 2205/3379* (2013.01); *A61M 2205/3553* (2013.01); *A61M 2205/52* (2013.01); *A61M 2205/6018* (2013.01); *A61M 2209/088* (2013.01)

(58) Field of Classification Search
CPC ... A61M 1/0697; A61M 1/069; A61M 1/0693
See application file for complete search history.

(56) References Cited

U.S. PATENT DOCUMENTS

| | | |
|---|---|---|
| 4,311,141 A | 1/1982 | Diamond |
| 4,768,547 A | 9/1988 | Danby et al. |
| 4,821,580 A | 4/1989 | Jomtsma |
| 5,542,921 A | 8/1996 | Meyers et al. |
| 5,634,468 A | 6/1997 | Platt et al. |
| 5,658,133 A | 8/1997 | Anderson et al. |
| 5,810,772 A | 9/1998 | Niederberger |
| 5,827,191 A | 10/1998 | Rosenfeld |
| 6,273,868 B1 | 8/2001 | Nordvik |
| 6,287,252 B1 | 9/2001 | Lugo |
| 6,328,082 B1 | 12/2001 | Lafond |
| D459,233 S | 6/2002 | Young |
| 6,440,100 B1 | 8/2002 | Prentiss |
| 6,547,756 B1 | 4/2003 | Greter et al. |
| 6,579,258 B1 | 6/2003 | Atkin et al. |
| 6,712,785 B2 | 3/2004 | Morton et al. |
| 6,840,918 B1 | 1/2005 | Britto et al. |
| 7,201,735 B2 | 4/2007 | Atkin et al. |
| 7,223,255 B2 | 5/2007 | Myers et al. |
| 7,621,797 B1 | 11/2009 | Hershkovich |
| 7,824,363 B2 | 11/2010 | Myers |
| 7,972,297 B2 | 7/2011 | Bryan et al. |
| 7,988,661 B2 | 8/2011 | Silver et al. |
| 8,057,425 B1 | 11/2011 | Myers et al. |
| 8,070,715 B2 | 12/2011 | Quackenbush et al. |
| 8,070,716 B2 | 12/2011 | Sutrina et al. |
| 8,262,606 B2 | 9/2012 | Greter et al. |
| 8,282,596 B2 | 10/2012 | Greter et al. |
| 8,353,865 B2 | 1/2013 | Thilwind et al. |
| 8,357,116 B2 | 1/2013 | Simdon |
| 8,376,986 B2 | 2/2013 | Van Schijndel et al. |
| 8,671,701 B2 | 3/2014 | McKendry |
| 8,684,961 B2 | 4/2014 | Gottenbos et al. |
| 8,801,495 B1 | 8/2014 | Guindon |
| 9,050,404 B2 | 6/2015 | Silver et al. |
| 9,162,016 B2 | 10/2015 | Geddes |
| 9,173,587 B2 | 11/2015 | Van Schijndel et al. |
| 9,199,017 B2 | 12/2015 | Greter |
| 9,278,167 B2 | 3/2016 | Aalders et al. |
| 10,722,624 B2 * | 7/2020 | Makower .............. A61M 1/064 |
| 2003/0191433 A1 | 10/2003 | Prentiss |
| 2004/0024351 A1 | 2/2004 | Greter et al. |
| 2004/0101414 A1 | 5/2004 | Gharib et al. |
| 2004/0127845 A1 | 7/2004 | Renz et al. |
| 2005/0059928 A1 | 3/2005 | Larsson |
| 2005/0131332 A1 | 6/2005 | Kelly et al. |
| 2005/0234370 A1 | 10/2005 | Beal et al. |
| 2006/0106334 A1 | 5/2006 | Jordan et al. |
| 2008/0045888 A1 | 2/2008 | Edwards et al. |
| 2008/0177224 A1 | 7/2008 | Kelly et al. |
| 2008/0243059 A1 | 10/2008 | Yamashita et al. |
| 2009/0024080 A1 | 1/2009 | Rohrig |
| 2010/0010682 A1 | 4/2010 | Zhou |
| 2010/0106082 A1 | 4/2010 | Zhou |
| 2010/0217148 A1 | 8/2010 | Binder |
| 2011/0071466 A1 | 3/2011 | Silver et al. |
| 2011/0196291 A1 | 8/2011 | Vischer et al. |
| 2011/0245763 A1 | 10/2011 | Myers |
| 2011/0270162 A1 | 11/2011 | Guo |
| 2012/0101575 A1 | 4/2012 | Horne et al. |
| 2012/0277636 A1 | 11/2012 | Blondheim et al. |
| 2012/0277728 A1 | 11/2012 | Weber et al. |
| 2013/0023821 A1 | 1/2013 | Khalil et al. |
| 2013/0123688 A1 | 5/2013 | Bosman et al. |
| 2013/0131665 A1 | 5/2013 | Silver et al. |
| 2013/0177455 A1 | 7/2013 | Kamen et al. |
| 2014/0066734 A1 | 3/2014 | Zdeblick |
| 2014/0378895 A1 | 12/2014 | Barack |
| 2014/0378946 A1 | 12/2014 | Thompson et al. |
| 2015/0065994 A1 | 3/2015 | Fridman et al. |
| 2015/0100016 A1 | 4/2015 | Liao |
| 2015/0148709 A1 | 5/2015 | Mardiks et al. |
| 2015/0196247 A1 | 7/2015 | Lau |
| 2015/0292500 A1 | 10/2015 | Girard et al. |
| 2016/0015876 A1 | 1/2016 | Tattersfield et al. |
| 2016/0206794 A1 * | 7/2016 | Makower .......... A61M 1/06935 |
| 2016/0256618 A1 | 9/2016 | Embleton |
| 2017/0173232 A1 * | 6/2017 | Chang .............. A61M 1/06935 |

FOREIGN PATENT DOCUMENTS

| | | |
|---|---|---|
| EP | 2456482 B1 | 11/2016 |
| EP | 3151876 B1 | 11/2017 |
| GB | 2342446 A | 4/2000 |
| JP | 2005279044 | 10/2005 |
| RU | 2012 107356 | 5/2012 |
| WO | WO1996022116 | 7/1996 |
| WO | WO 2000/57934 | 10/2000 |
| WO | WO2001054488 | 8/2001 |
| WO | WO2011010255 | 1/2011 |
| WO | WO2011144984 A | 11/2011 |
| WO | WO2012037848 | 3/2012 |
| WO | WO2012037848 A1 | 3/2012 |
| WO | WO 2013076055 | 5/2013 |
| WO | WO2013088310 | 6/2013 |
| WO | WO 2013/187763 | 12/2013 |
| WO | WO2013184004 | 12/2013 |
| WO | WO2015120321 | 8/2015 |

OTHER PUBLICATIONS

Double Electric Breast Pump/Dr. Brown's, http://www.drbrownsbaby.com/breastfeeding-product/breast-pumps/double-electric, May 15, 2014.

* cited by examiner

BREAST PUMP SYSTEM WITH COLLECTION CONTAINER

This application is a Continuation of U.S. Ser. No. 16/050,201, filed Jul. 31, 2018, which is a continuation of PCT/US17/17112, filed Feb. 9, 2017, which claims priority to Provisional Application Nos. 62/450,528, filed Jan. 25, 2017, 62/442,008, filed Jan. 4, 2017, 62/421,263, filed Nov. 12, 2016, and 62/293,480, filed Feb. 10, 2016, the contents of each of which are incorporated herein by reference in their entirety; and This application is a Continuation-In-Part of U.S. Ser. No. 16/934,380, filed Jul. 21, 2020, which is a Continuation of U.S. Ser. No. 16/667,749, filed Oct. 29, 2019, now U.S. Pat. No. 10,722,624, which is a Continuation of U.S. Ser. No. 15/180,345, filed Jun. 13, 2016, now U.S. Pat. No. 10,688,229, which is a Continuation of PCT/US2015/041257, filed Jul. 21, 2015, which claims priority from Provisional Application U.S. Ser. No. 62/027,685, filed Jul. 22, 2014, the contents of each of which are incorporated herein by reference in their entirety.

FIELD OF THE DISCLOSURE

The present disclosure generally relates to portable breast pump systems and methods for collecting milk from a breast of a nursing mother.

BACKGROUND OF THE DISCLOSURE

As more women become aware that breastfeeding is the best source of nutrition for a baby, and also offers health benefits to the nursing mother, the need is increasing for breast pump solutions that are user-friendly, quiet, discrete and versatile for use by a nursing mother in various situations. This is particularly true for the working mother, who is away from the home for eight to ten hours or more and needs to pump breast milk in order to have it available for her baby, but it is also a requirement for many other situations where the mother is away from the privacy of the home for an extended period, such as during shopping, going out to dinner or other activities.

Although a variety of breast pumps are available, a number are awkward and cumbersome, requiring many parts and assemblies and being difficult to transport. Hand pump varieties that are manually driven are onerous to use and can be inconvenient to use. Some powered breast pumps require an AC power source to plug into during use. Some systems are battery driven, but draw down the battery power fairly rapidly as the motorized pump continuously operates to maintain suction during the milk extraction process. Many of the breast pumps available are clearly visible to an observer when the mother is using it, and many also expose the breast of the mother during use.

There is a continuing need for a small, portable, self-powered, energy efficient, wearable breast pump system that is easy to use, that mimics natural nursing, and is discrete by not exposing the breast of the user and nearly unnoticeable when worn.

To ensure that the nursing baby is receiving adequate nutrition, it is useful to monitor the baby's intake. It would be desirable to provide a breast pump system that easily and accurately monitors the volume of milk pumped by the system, to make it convenient for the nursing mother to know how much milk has been extracted by breast pumping. It would also be desirable to track milk volume pumped per session, so that the volume of milk contained in any particular milk collection container can be readily known.

There is a continuing need for a breast pump system that is effective and convenient to use. The present disclosure addresses these and other needs.

SUMMARY OF THE DISCLOSURE

Briefly and in general terms, the present disclosure is directed toward breast pump systems or methods. The system includes breast contacting structure and a collection or storage container or assembly, and structure that delivers milk from a breast to the collection assembly. The method involves pumping milk from a breast and delivering the pumped milk into the collection assembly or storage container. In one particular aspect, the breast pump system responds in real time to optimize pumping action for a particular user during a particular pumping session.

According to one aspect of the present disclosure, a system for pumping milk from a breast includes one or more of: a skin contact member or flange configured to form a seal with the breast; a conduit in fluid communication with and connected to the skin contact member; a driving mechanism configured to establish a vacuum profile within the conduit; an external shell; a milk collection container; and a non-transitory computer readable medium having stored thereon instructions executable by a computing device to cause the computing devices to perform functions associated with and directed by the instructions; wherein the external shell comprises a compartment; wherein the skin contact member, the conduit and the driving mechanism are received in the compartment of the external shell; wherein the milk collection container is positionable within the shell; and wherein the system is shaped and configured to be contoured to the breast of a user.

In one or more embodiments, the system can include one or more of structure configured to address fluid ingress, pinch protection structure, a flex-tube structured to accomplish efficient and predictable pumping of fluid and the creation of desirable pressure profiles, and cooperating structure for fluid collection secure attachment and removal.

In various embodiments, the storage container can be specifically configured to prevent kinking and for durability and handling. The storage container can be designed to hold, accept or retain milk or other fluids. A flow feature can be incorporated into the storage container in the form of a scallop structure, valves and materials can be chosen to facilitate removing air or gases, tabs and wings can be provided for handling, and structure adapted for the removal of milk from a collection assembly.

In various of the disclosed embodiments, the system defines a breast profile. The natural breast profile is contemplated to fit comfortably and conveniently into a bra of a user and to present a natural look. As such, the profile is characterized by having a non-circular base. Moreover, like natural breasts, the profile of the device or system is contemplated to define one or more asymmetric curves and off-center inertial centers. In one aspect, the system defines a breast enhancement system for enlarging the appearance of the user's breast.

In at least one embodiment, the system functions by operating a control system that tracks internal pressure of the system against a known waveform. In this regard, the waveform can be a vacuum waveform indicative of pressures applied to a breast, and can define a sine wave fluctuating between about 60 mmHg of vacuum to a vacuum from about 120 mmHg to about 250 mmHg, or other desirable or useful waveform.

In one or more embodiments, the system includes a controller that accomplishes real time pressure control inside the system.

In one or more embodiments, the system includes a controller providing automated compliance sensing and response.

In one or more embodiments, the system includes a non-contact pressure sensing arrangement that does not touch the skin or the milk inside the tube while accurately determining internal pressure of the tube.

In one or more embodiments, the system includes one or more controllers that automatically detects one or more of letdown, overfill and flow.

In one or more embodiments, the system is disabled when the flange is not placed in an operating position.

In one or more embodiments, the system can be adapted to visualize a user's data and trends as it relates to volume (from each breast and total), and number of sessions on several dimensions (per day, per week and per month). Data and analytics can also be provided on pumping session.

In at least one embodiment, the flange or skin contact member, the conduit, the driving mechanism, the external shell and the milk collection container are all contained within a cup of a brassiere. In other embodiments, the container need not be contained within the housing, and the pump need not be in a cup of a brassiere, but can be unsupported or supported by itself or by other clothing or a nursing tank top or a band surrounding the user's body.

In at least one embodiment, the system is battery powered, the system comprising a battery, wherein the battery is received in the compartment of the external shell.

In at least one embodiment, the milk collection container comprises a one-way valve that permits milk inflow into the milk collection container but prevents milk backflow from the milk collection container to the conduit. In one embodiment, the collection container or container assembly includes an extra part, valve or fitment that is attached thereto and facilitates creating a seal with the container to establish a closed system. In one embodiment, the milk container can include a one-way valve that cannot be removed without destroying milk container or valve function. The valve can assume a myriad of shapes and kinds including an umbrella valve, a duckbill valve, a ball valve or other valve. Moreover, in one or more embodiments, the container can be flexible or rigid, or disposable or reusable.

According to another aspect of the present disclosure, a system for pumping milk from a breast includes one or more of: a flange or skin contact member configured to form a seal with the breast; a conduit in fluid communication with and connected to the skin contact member; a driving mechanism configured to establish a vacuum profile within the conduit by cyclically compressing and allowing decompression of a portion of the conduit; and an external shell containing the conduit and the driving mechanism and supporting the skin contact member.

In at least one embodiment, the system further includes a milk collection container, wherein the milk collection container is in fluid communication with the conduit.

In at least one embodiment, the skin contact member includes: a breast contact portion configured and dimensioned to fit over and form a seal with a portion of the breast; and a nipple receiving portion extending from the breast contact portion.

According to another aspect of the present disclosure, a method of operating a system for pumping milk includes one or more of: providing the system comprising a skin contact member configured to form a seal with the breast, a conduit in fluid communication with and connected to the skin contact member; a driving mechanism including a compression member configured to compress and allow decompression of the conduit in response to inward and outward movements of the compression member, a sensor, and a controller configured to control operation of the driving mechanism; sealing the skin contact member to the breast; operating the driving mechanism to generate predetermined pressure cycles within the conduit; monitoring by the controller of at least one of position and speed of movement of the compression member relative to the conduit; measuring or calculating pressure within the conduit; maintaining or modifying motion of the compression member as needed, based upon feedback from the calculated pressure and at least one of force, position and speed of movement of the compression member, to ensure that the predetermined pressure cycles continue to be generated.

In at least one embodiment, the predetermined pressure cycles comprise extraction pressure cycles, and the controller increases a stroke distance of the compression member relative to an amount of milk entering the conduit, to maintain predetermined pressures during the extraction pressure cycles.

In at least one embodiment, the predetermined pressure cycles comprise latch cycles, wherein upon determination that milk has entered the conduit or after a predetermined period of time, the controller operates the compression member to achieve predetermined extraction pressure cycles, wherein the predetermined extraction cycles differ from the predetermined latch cycles by at least one of maximum suction level, cycle frequency or waveform shape. Moreover, in one or more embodiments, the system includes structure or functions to recognize when a user is done pumping, or includes structure or functions such that when there is a loss of vacuum recognition which allows the user to easily end a pumping session by simply pausing and pulling the device off of the breast. Additionally, in one or more embodiments, the system can include an auto-purge function or an accelerometer functioning as gesture recognition so that the device can interpret what the user is attempting to accomplish.

According to another aspect of the present disclosure, a system for pumping milk includes one or more of: a flange or skin contact member configured to form a seal with a breast; a conduit in fluid communication with and connected to the skin contact member; a driving mechanism including a compression member configured to compress and allow decompression of the conduit in response to inward and outward movements of the compression member; a sensor; and a controller configured to control operation of the driving mechanism; wherein upon sealing the skin contact member to the breast, the controller operates the driving mechanism to generate predetermined pressure cycles within the conduit, monitors at least one of position and speed of movement of the compression member relative to the conduit, measures or calculates pressure within the conduit based upon signals received from the sensor, and maintains or modifies motion of the compression member as needed, based upon feedback from the calculated pressure and at least one of force, position and speed of movement of the compression member, to ensure that the predetermined pressure cycles continue to be generated.

These and other features of the disclosure will become apparent to those persons skilled in the art upon reading the details of the systems and methods as more fully described below.

DETAILED DESCRIPTION OF THE DISCLOSURE

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a sensor" includes a plurality of such sensors and reference to "the pump" includes reference to one or more pumps and equivalents thereof known to those skilled in the art, and so forth.

The publications discussed herein are provided solely for their disclosure prior to the filing date of the present application. The dates of publication provided may be different from the actual publication dates which may need to be independently confirmed.

Various details of the present system can be found in PCT Application Nos. PCT/US15/41257, PCT/US15/41271, PCT/US15/41277, and PCT/US15/41285 each filed Jul. 21, 2015, and PCT/US15/50340 filed Sep. 16, 2015, each of which are hereby incorporated herein, in their entireties, by reference thereto.

Figure 1A:
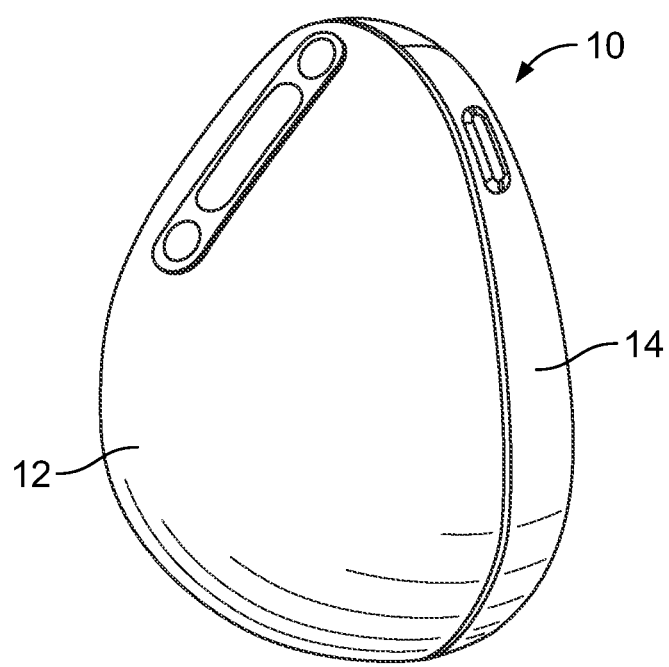
FIG. 1A shows a perspective view of a breast pump system according to an embodiment of the present disclosure.
Figure 1B:
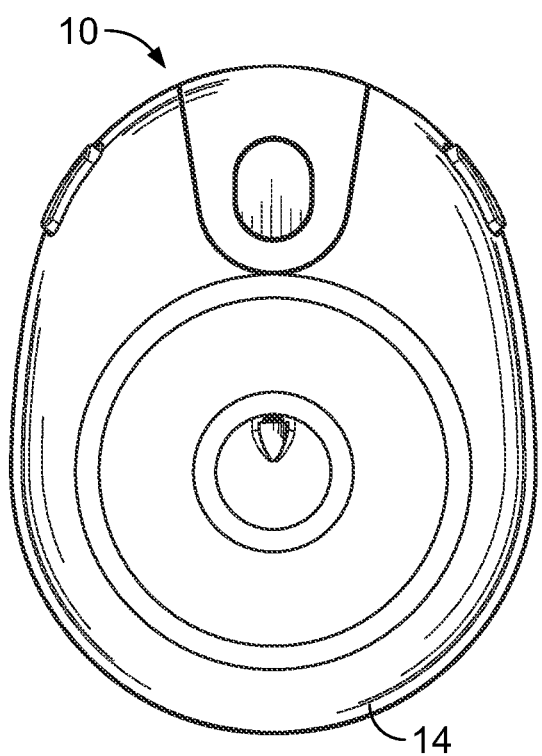
FIG. 1B is a rear view, depicting the flange of the pump system of FIG. 1A.

FIGS. 1A-B are perspective and back views of a breast pump system 10 according to an embodiment of the present disclosure. The breast pump system 10 can include one or more of the below introduced or described features or functions, or a combination thereof. The housing or outer shell 12 of system 10 can be shaped and configured to be contoured to the breast of a user and to thus provide a more natural appearance when under the clothing of the user. As can be appreciated from the figures, the system can define a natural breast profile. The natural breast profile is contemplated to fit comfortably and conveniently into a bra of a user and to present a natural look. As such, the profile is characterized by having a non-circular base unlike that embodied in a generally dome-shaped configuration. Extending from the base are curved surfaces having asymmetric patterns. Moreover, like natural breasts, the profile of the device or system is contemplated to define one or more asymmetric curves and off-center inertial centers. Various natural breast shapes can be provided to choose from to the tastes and needs of a user. An opposite side of the pump system 10 is configured with a flange 14 which is sized and shaped to engage a breast of a user. The flange 14 is contoured to comfortably fit against a wide range of user's bodies and to provide structure for sealingly engaging with breast tissue. In one particular embodiment, the flange 14 can form generally rigid structure, and alternatively or additionally unlike a standard flange can lack sharp edges or a lip portion against which breast tissue might be engaged during use. In this regard, the flange includes surfaces that extend outwardly from a nipple receiving portion of the flange to engage breast tissue, thus providing extra surface area for comfortably contacting tissue. Various approaches are contemplated to the flange with respect to a user's nipple. One approach involves aligning a horizontal line formed within the flange structure a bit higher than center with the rationale that the perspective of the mother is from above. This perspective allows the user to better align the breast with the horizontal line to better center the nipple in the actual center of a nipple receiving portion of the flange, thus offsetting any tendency to aim/line up low associated with centered lines because the user's perspective is from above the line and also because the device is pivoted into place in certain instances.

Figure 2:
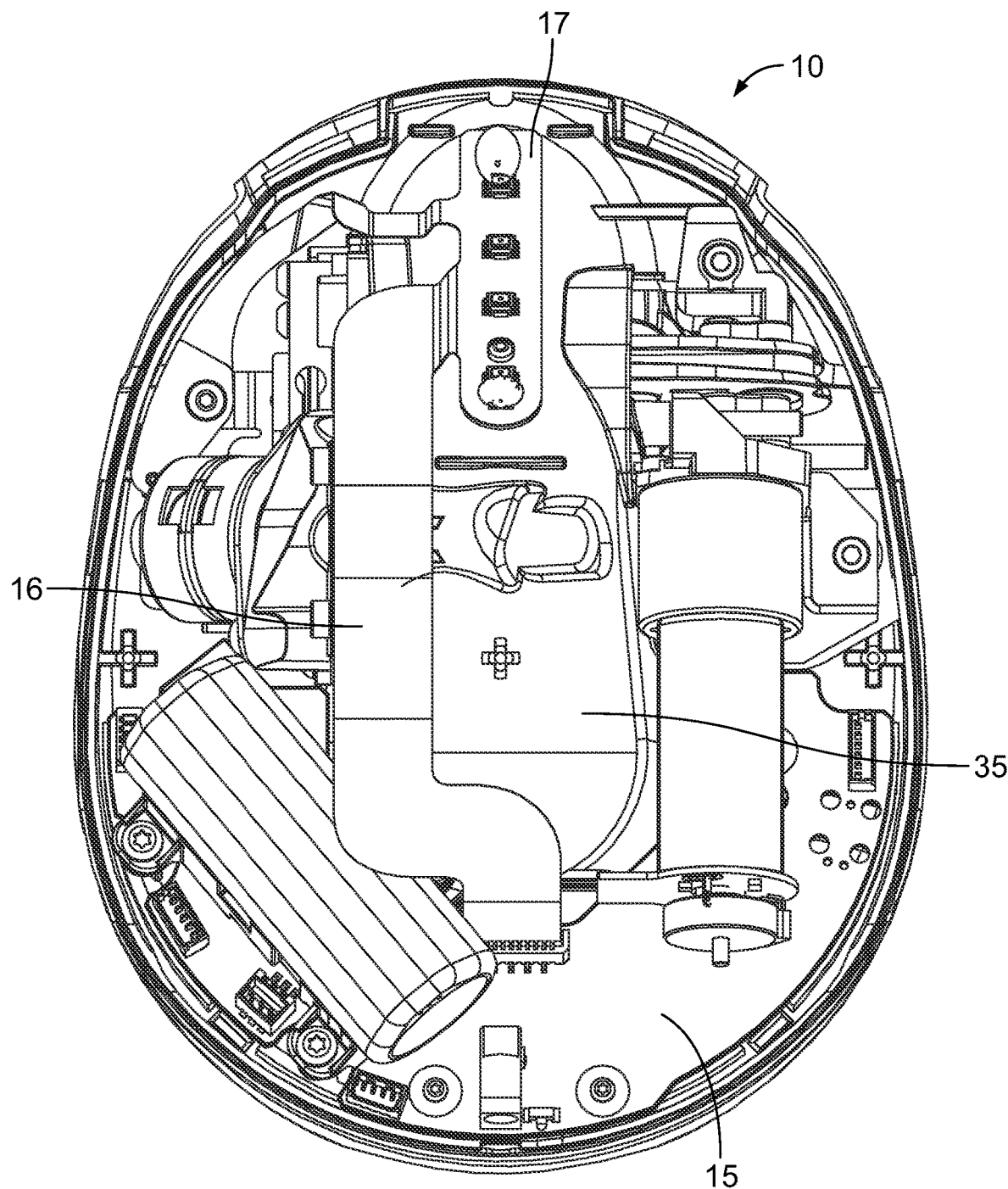
FIG. 2 shows a front view of the system of FIG. 1 with the shell removed.

FIG. 2 is a front view of the system 10 of FIG. 1, with the housing or outer shell 12 having been removed and made transparent to show components otherwise covered by the housing 12. In particular, with the housing 12 removed, various electronic components can be identified. The system controller is embodied in a circuit board 15 that is in communication with a flex-circuit 16, each cooperating to connect to and control various electro-mechanical components of the system 10. A control panel 17 is in electronic communication with the controller via the flex-circuit 16 and provides the user with the ability to power the system on and off as well as to alter functioning. One or more motors 44, 46 are further provided and controlled electronically by the system to effect manipulation of actuators (described below) operating on a conduit or flex-tube 32 (See FIGS. 4 and 5). A battery 48 is included to provide a rechargeable power source and is configured to be plugged into a power source for charging. Further, there is provided a load cell assembly 54 that is configured to provide a pressure sensing function as described below. It is contemplated that at least in one embodiment, the conduit or flex-tube 32 is oriented to run from inferior to superior relative to the nipple of a breast when the user is upright.

Figure 3:
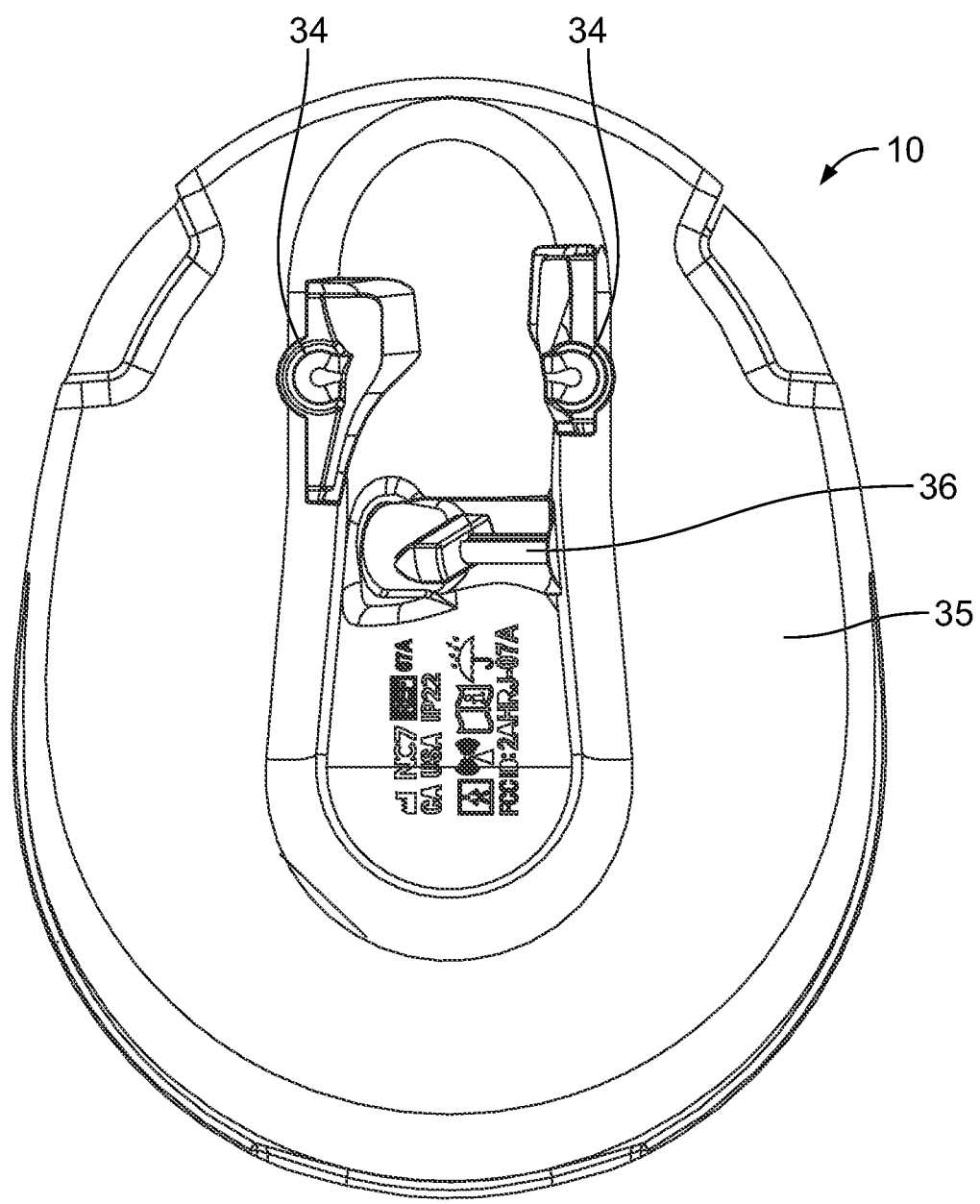
FIG. 3 depicts a back view of the system of FIG. 1 with the flange removed.

FIG. 3 shows an opposite side of the system 10 with the flange 14 removed to illustrate more details of the pumping function. The conduit or flex-tube 32 (See FIGS. 4-6) includes generally spherically shaped connectors 33 that are sized and shaped to be removably received in recesses 34 formed in a pump chassis 35. The connectors 33 are designed to automatically engage with moving motor paddles without the user being aware or having to make adjustments, or assemble parts. The pump chassis 35 functions to support the electronic and electro-mechanical structures of the system 10 (See also FIG. 2). It also provides spacing for a pinching actuator 36 that is configured to be advanced and retracted toward and away from the conduit or flex-tube 32 as described further below. Other pumping action is accomplished through the engagement of the conduit or flex-tube 32 with recesses 34 by a compression and expansion member 38 (See FIG. 7A). Embossed engraving is further provided within a well formed in the chassis 35, the engraving providing product and other information relevant to the breast pump. In this way, certain adhesive labels need not be applied to the breast pump structure.

In general, real-time pressure control can be managed by a controller of the system 10. The controller tracks pressure and moves a pump motor either in or out to influence the pressure in the direction of its choosing. By way of oscillating motion of the motor, the pump can be configured to pull on the connectors 33 of the conduit or flex-tube 32 structure to increase its volume. If there is vacuum in the system 10 that vacuum can be increased as the volume of the tube increases. Pushing in the tube decreases its volume. This in turn causes the vacuum level to decrease in the tube, and can cause a relative positive pressure if vacuum decreases enough. The pump controller applies these principles, sensing the current pressure and then nudging a compression member or paddle of the motor assembly in a direction required to generate a pressure target. By doing this repeatedly in real time, the system can create a controlled vacuum waveform that matches waveforms desired to be applied to a user's nipple.

The pump can slowly pull the compression member or paddle out until it hits a pre-determined target. Should the paddle be moved to the end of its range without being able to generate a desired vacuum, the system will be purged to generate more vacuum potential. The purge functions to push material out of the system to create a strong vacuum potential. It accomplishes this by first closing a pinch on the conduit or flex-tube or closing off the flex-tube with a flap, dam, etc., then evacuating the flex-tube, for example, by pushing closed the paddle, which forces volume out of the flex-tube and any fluid or air that was inside that volume is also ejected through the one-way valve and into the collection receptacle. When the paddle retracts again, it can then generate much higher vacuum as contents of the tube had been previously purged. Once a higher vacuum can be generated, the system can open the pinch valve so that the desired vacuum profile can be applied to a breast and desired pressure waveform can be produced.

When the system is filled with air, it is very compliant such that a large change in motor positioning makes only a small change in vacuum. When the system is filled with fluid on the other hand, a small change in motor positioning makes a big change in vacuum. In one particular approach, an encoder including a plurality of spaced magnets is associated with the motor. The magnets can be placed along a periphery of a generally disc shaped encoder with the magnets oriented parallel to the axis of rotation of the encoder. One or more hall effect sensors can be configured on or surface mounted to the circuit board 15 and positioned to read the motion and position of the magnets. In this way, the position of the motor can be determined and monitored. Thus, a challenge can be to configure the system so that it is stable when the system is responsive, and effective when it is not as responsive. One contemplated approach is to tune the controller for a relatively rigid system and to input unit-less quantities that move the motor in required directions where the amplitude of which is modified depending on the output of the system. Accordingly, a cascade controller can be created to grow an input wave if system output is smaller than desired to hit pressure targets and can be shrunk if the system output is larger than required. This can be accomplished in real time by observing output verses input. In this way, the controller can be continuously adjusting target waveforms. Top half and bottom half waveforms can have independent control which facilitates centering waveforms in an effective manner, and results in a system that is both very accurate and quick to adjust.

The system can further be provided with automated letdown detection. The pump can sense when it is full of fluid and responds accordingly by switching between pumping and letdown when fluid has begun to flow. In one approach an algorithm incorporated into the system can operate to look at the ratio of maximum and minimum of a target wave in the pump and compare that against the output of the pump. The result is a unit-less but very reliable sensing of system compliance. This can be tuned to trigger an internal event when the compliance crosses some known values that represent when the system is full of fluid. Any other measurement of compliance can be used in an equivalent way.

In another approach to letdown detection, it is noted that pushing a tube of air does not generate the same forces as pushing a tube of fluid. Tracking the force generated during a purge can also give a strong indication of when the system is full of fluid. An event can be generated to track this such that when the force of a purge crosses some known threshold the system can be said to be full of fluid rather than air. This approach may involve less tracking of data and less tuning that is subject to change with pump design or breast tissue. In yet another approach, letdown detection can be based upon tracking flow. That is, when flow begins, letdown must have occurred and when a small volume of flow has been collected the system can switch to pumping. Further, letdown can be tracked by looking at the relative rate of change of vacuum measured to motor position. Note that this relative rate of change is a measurement of compliance. As this ratio goes up in magnitude, it can be concluded that the system is filling with fluid.

Figure 4:
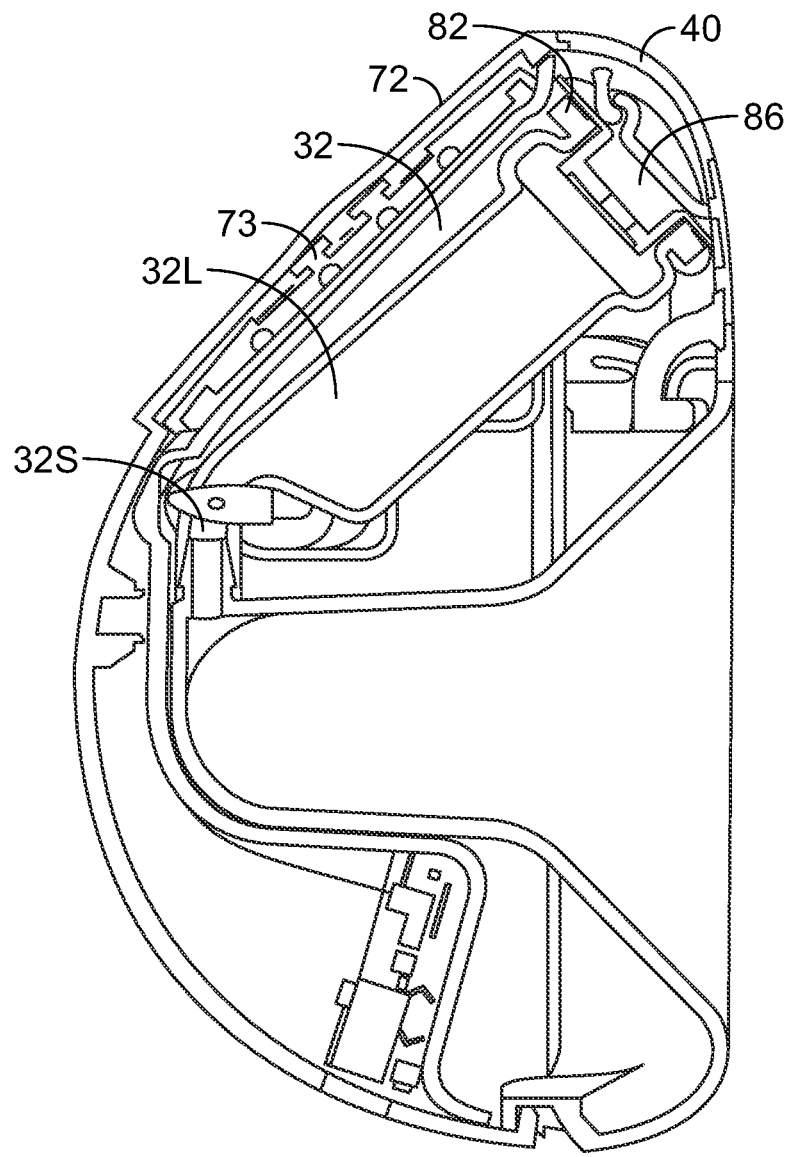
FIG. 4 is a cross-sectional side view of the system of FIG. 1.
Figure 5:
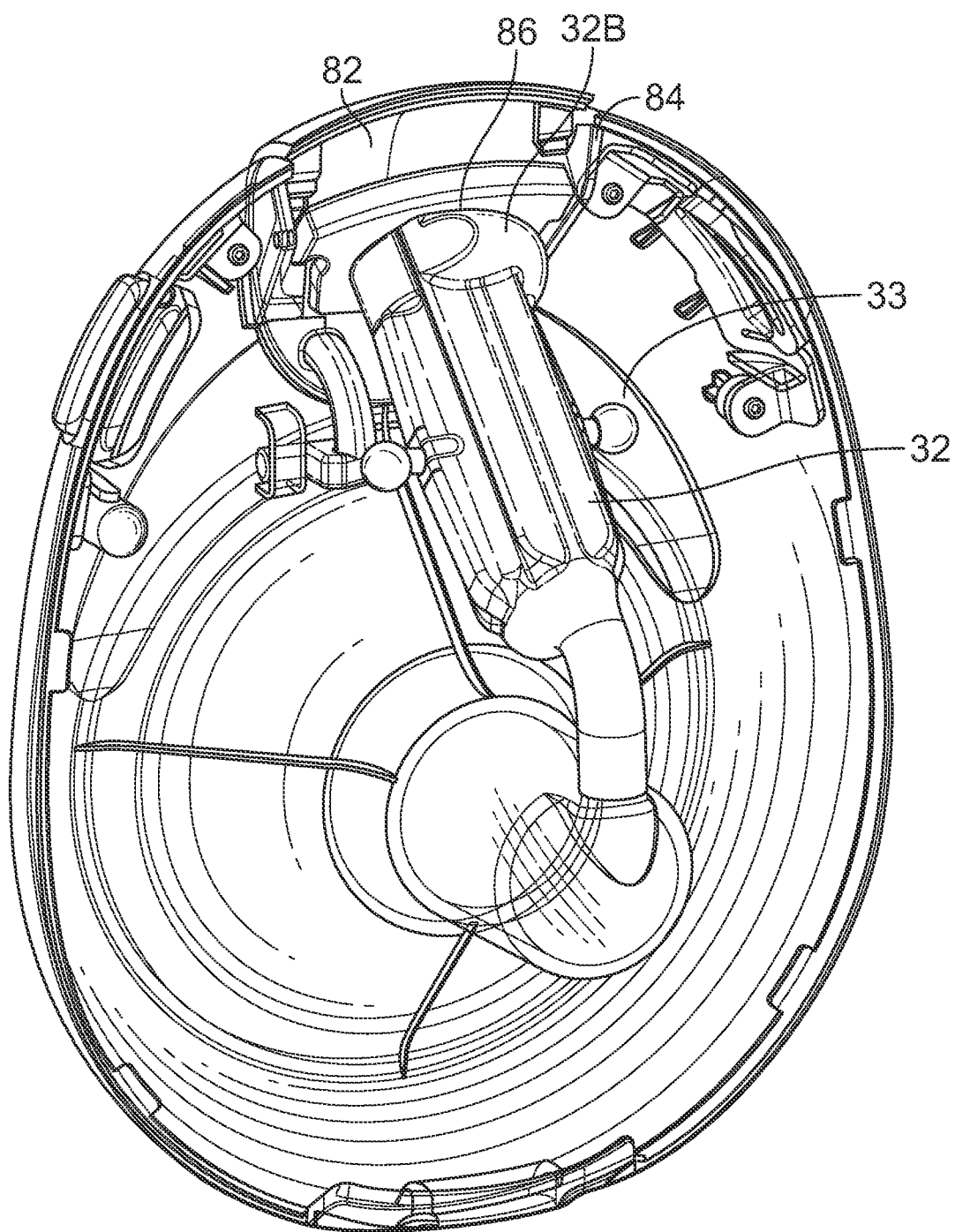
FIG. 5 is an inside view of the system of FIG. 1, depicting the flex conduit of the pump assembly.

FIG. 4 illustrates a cross-section of components of a system 10 according to an embodiment of the present disclosure. Flex-tube or conduit 32 (isolated in FIG. 5) includes a large conduit portion 32L that is relatively larger in cross-sectional inside area than the cross-sectional inside area of small conduit portion 32S. The large conduit portion 32L terminates with an opening sized for cleaning and is generally sized to accept a small finger tip. Although both portions 32S and 32L are shown as tubular portions, the present disclosure is not limited to such, as one or both portions could be shaped otherwise. When tubular, the cross-sections may be oval, square, other polyhedral shape, non-symmetrical, or non-geometric shape. Further, the flex-tube 32 can include an enlarged bulbous portion 32B configured near a terminal end of the large conduit portion 32L that is provided to help accommodate system hysteresis.

Figure 6A:
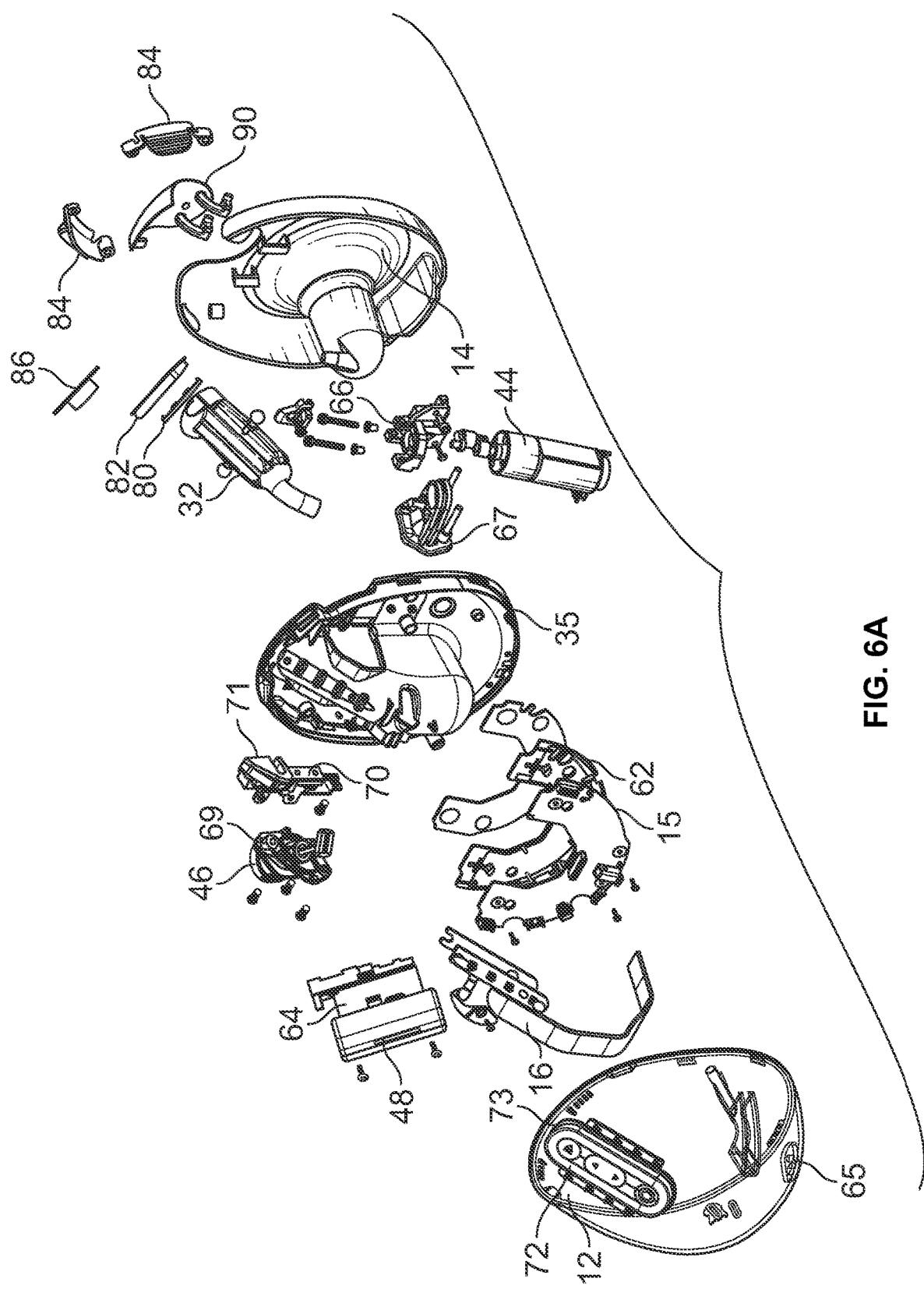
FIG. 6A is an exploded view of the system of FIG. 1, depicting mechanical components of the system.
Figure 7A:
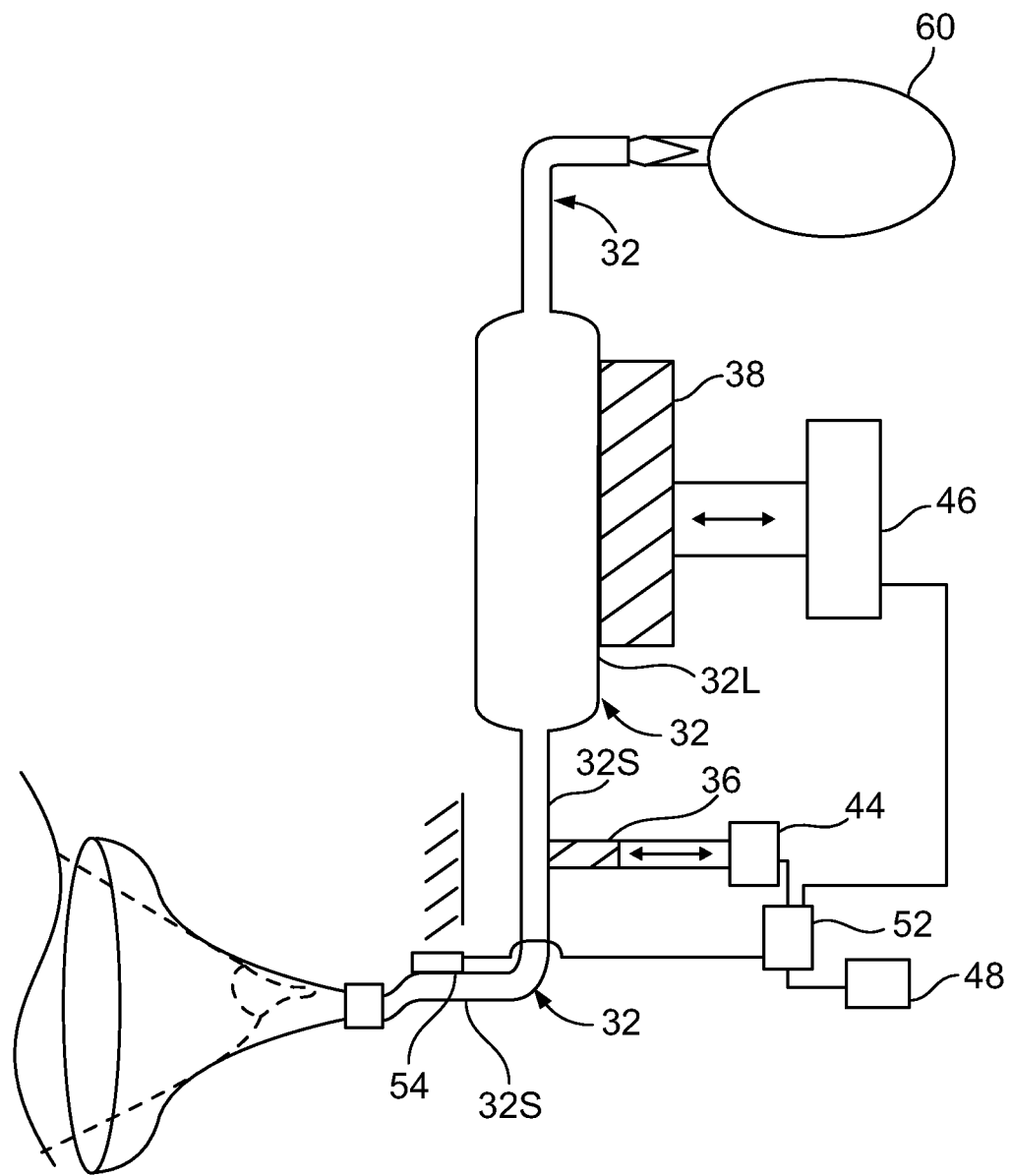
FIG. 7A is a schematic representation, depicting operational components of the system.

FIG. 6A depicts an exploded view of structural and mechanical components of the system 10. Configured between the housing 12 and flange 14 is the chassis 35. Notably, the chassis can be configured to snap into engagement with the housing 12. Moreover, in a preferred embodiment, the chassis 35 supports directly or indirectly all of the pump components. In particular, a PCB controller mount 62 is supported by the chassis 35 and is configured to be connected to and support the circuit board 15 (See also FIG. 2). A battery bracket 64 is also supported by the chassis 35 and is sized and shaped to receive a rechargeable battery 48 assembly that powers the system 10. A cover jack 65 is further included to provide access to the battery assembly and for accepting a power cord connector (not shown). Motor mounting 66 and motor receiver structure 67 is also supported by the chassis 35 and are configured to receive and support the system motor which is powered by the battery and which functions to move actuators operating on the conduit or flex-tube 32. Also supported by the chassis 35 are an actuator bracket 69, and a load cell bracket 70 and load cell receiver 71. Moreover, user interface panel can include a button membrane 72 and a button membrane housing 73 each supported on the housing 12 and placed in engagement with the flex-circuit 16 that provides the user with system control.

In order to connect the conduit or flex-tube assembly 32 to the system 10, there are provided a flex-tube ring 80 and a flex-tube collar 82. The flex-tube collar 82 is sized and shaped to be received into slots 84 on the flange. A fluid container fitment 86 (shown in isolation from the container) is sized and shaped to be received into the flex-tube collar 82. A door assembly 90 is attached to the flange 14 and configured to swing open and closed to both provide access to an interior of the system 10 as well as to support a robust connection between the fitment 86 and flex-tube collar 82. Accordingly, it is contemplated that in at least one embodiment, the collection or container assembly is supported and maintained in attachment by friction around a shaft of the conduit to the collection or container assembly, and partially by the door assembly 90 which can enclose and hold the collection or container assembly in place. In alternative embodiments, the breast pump assembly can omit a door assembly entirely. Thus, the flange itself can include structure for retaining the container assembly in place. Moreover, the door assembly or other structure that replaces the door assembly can be transparent so that a direct view to the container assembly is provided.

Figure 6B:
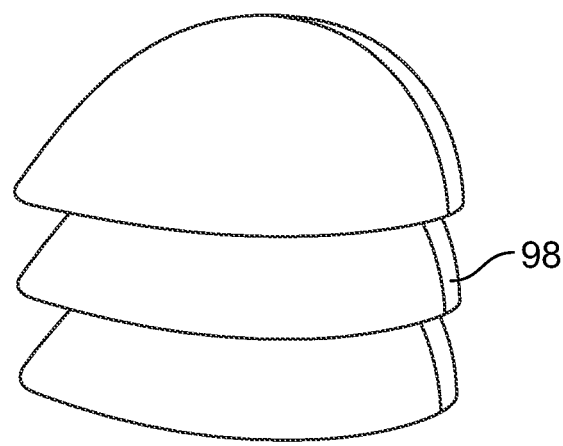
FIGS. 6B-D depict views of an alternative approach to housing structure.
Figure 6B:
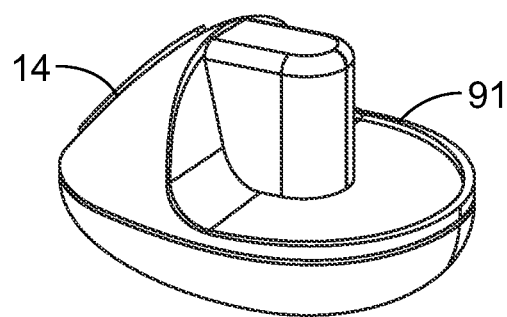
Figure 6C:
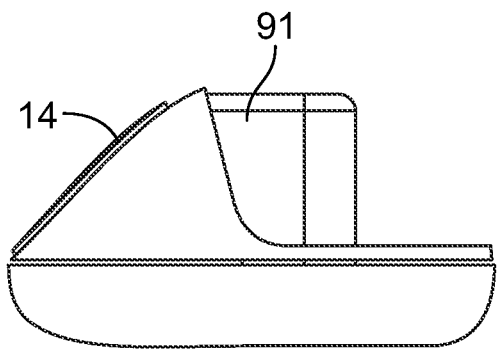
Figure 6D:
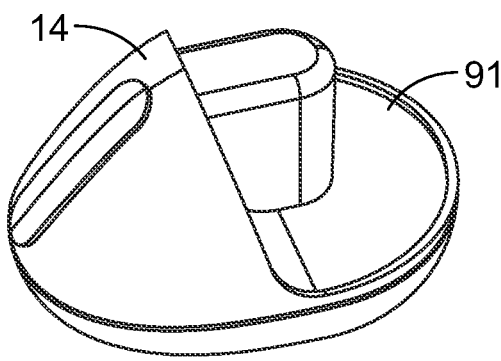
Figure 6E:
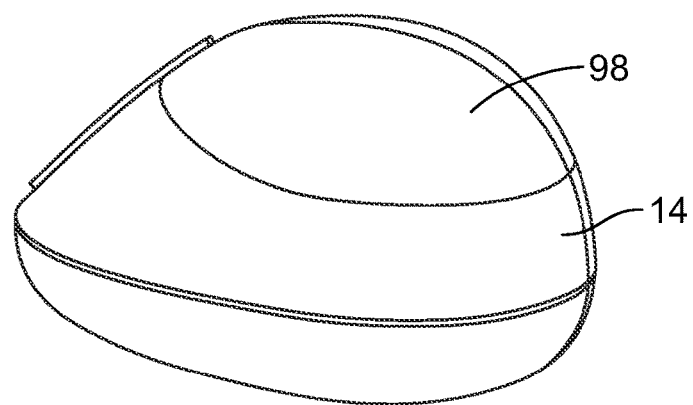
FIGS. 6E-G depict views of yet another alternative approach to housing structure.
Figure 6F:
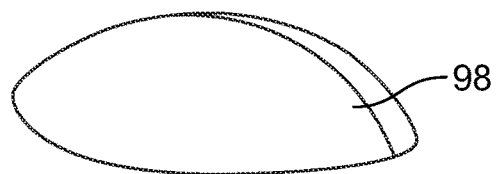
Figure 6F:
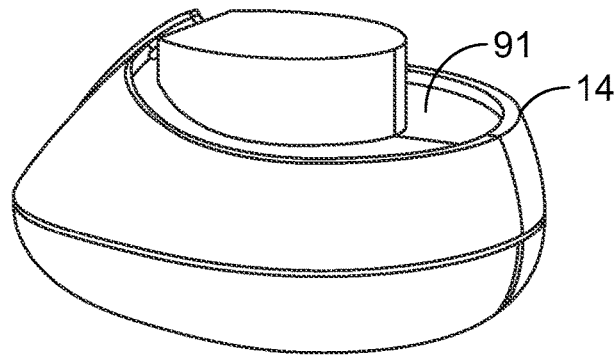
Figure 6G:
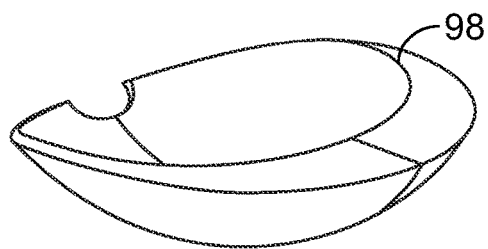
Figure 6H:
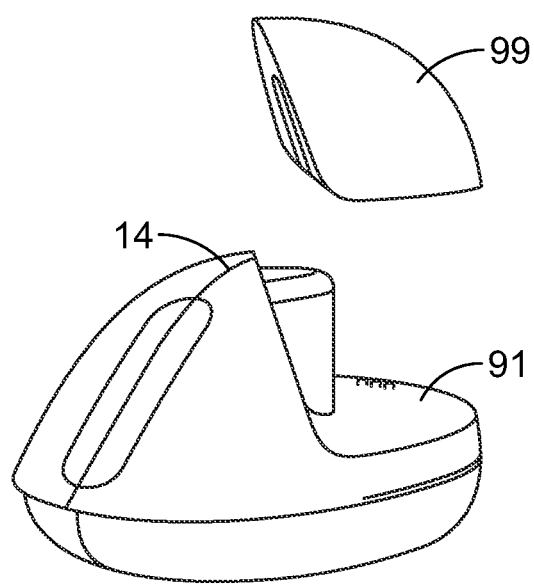
FIG. 6H is a perspective view, depicting a first approach to a system including a removable battery structure.
Figure 6I:
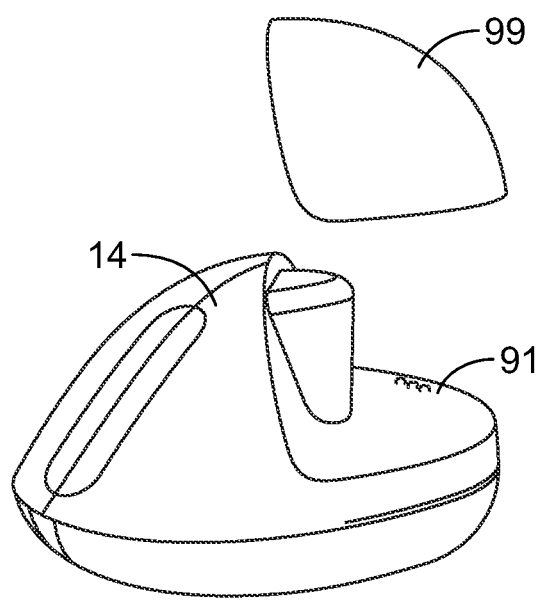
FIG. 6I is a perspective view, depicting a second approach to a system including a removable battery structure.
Figure 6J:
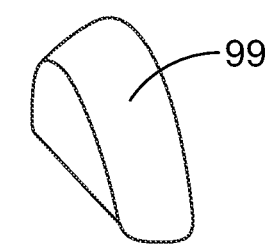
FIG. 6J is a perspective view, depicting a third approach to a system including a removable battery structure.
Figure 6J:
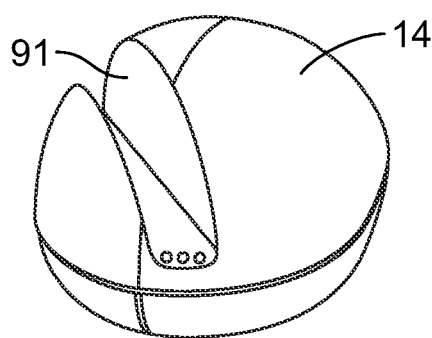

In alternative embodiments, the housing 14 is defined by an irregular shape that includes contours that track or mimic the internal components and structure of the pump system. In one particular approach as shown in FIGS. 6B-D, an outer surface of the housing 14 is characterized by an irregular shaped indentation 91, providing the outer surface with an irregular shape. Various differently shaped indentations 91 can be employed (See also FIGS. 6E-G). Various configurations of a separate breast cup skin or interface structure 98 is sized and shaped to fit over the housing 14 and indentation 91 to form a desired shape such as the breast shape depicted in the figures. It is noted that the breast pump system can work with or without the breast cup skin or interface structure. Alignment and attachment structure or holes can be further provided to facilitate the mating of the interface structure 91 with the housing 14 and the interface structure can assume a myriad of colors, textures and durometer to enhance or change tackiness, softness for security and outer feel in the bra. Various other breast and other shaped can also be provided.

In yet further combined or separate embodiments (See FIGS. 6H-J), the housing 14 can be adapted or configured to additionally or alternatively accommodate a replaceable battery. Here, the housing 14 includes various other shaped indentations 91 sized and shaped to accommodate the battery. In this approach, the battery includes its own attachable housing 99 that mates with the housing 14 indentation 91, the housing 14 covering other pumping structures. In one approach, mating features include flat, right-angled structures, and alignment and attachment holes and structures are further provided.

As shown schematically in FIG. 7, latching, pumping and extraction forces can be established by two compression members 36, 38 that are actively driven by motor drivers 44 and 46 respectively. Although more than two compression members could be used and one or more than two drivers could be used, the currently preferred embodiment uses two compression members respectively driven by two drivers as shown. A system controller or system software and/or firmware controls the action of the drivers in real time, responsive to pre-determined latching and production targets or schemes as detected by the pressure sensor or load cell assembly. The firmware can be written so that such targets can be approached at various speeds, sometimes relatively quickly and other times more slowly or gently to thereby provide multiple stimulation and expression levels. Thus, for example, latch can be achieved taking alternatively more gradual or quicker approaches, and there can be controls determining the level at which latch is achieved. Various levels of suction can be present during expression as well. Tubing portions 32S and 32L can be closed off, or substantially closed off by compression members 36 and 38, respectively. Moreover, such active pumping members can be configured to engage upon a tubing channel generally perpendicularly to the net flow of fluid or milk within the channel. Also, a pinch region of the tubing channel can be configured to open through passive recoil located next to a compression region of the tubing channel which opens through an assistive active support. Upon powering up the system 10 the compression member 36 opens and the compression member 38 begins to withdraw away and through its connection to structure such as the ball connector of the conduit or flex-tube 32 thereby gradually increases the suction level within tubing 32. When a predetermined maximum suction level is achieved (as confirmed by pressure readings taken from a pressure sensor, described below), the compression member 38 ceases its travel in the current direction, and either maintains that position for a predetermined period of time (or moves slightly in the same direction to compensate for decreasing suction as milk enters the system) when the operating mode of the system 10 has a predetermined time to maintain maximum suction, or reverses direction and compresses the tube 32L until the latch suction level is achieved. If the maximum suction level has not yet been achieved by the time that the compression member can be fully retracted away on the first stroke, then the compression member 36 again compresses the tube 32S to seal off the current vacuum level in the environment of the breast, and the compression member 38 fully compresses the tube portion 32L to squeeze more air out of the system. Then the compression member 36 reopens to fully open tube portion 32S and compression member carries out another stroke, again moving away to generate a greater suction level. This cycling continues until the maximum suction level is achieved. It is noted that it is possible in some cases to achieve the maximum suction level on the first stroke, whereas in other cases, multiple strokes may be required.

Upon achieving the maximum suction, the system may be designed and programmed so that the compression member 38 does not travel to its fullest possible extent in either direction to achieve the maximum and latch suction levels, so as to allow some reserve suction and pressure producing capability. When the maximum suction level has been achieved, and the pumping profile can return to latch vacuum, the compression member 38 advances compressing tubing portion 32L, thereby raising the vacuum in the tubing 32. Upon achievement of the latch suction vacuum, compression member 36 closes off the tubing 32S again to ensure that the latch vacuum is maintained against the breast, so that sufficient suction is maintained. At this stage, the compression member 38 again begins moving away to increase the suction level back to maximum suction, and compression member 36 opens to allow tube 32S to open and the breast 2 to be exposed to the maximum suction. Alternatively, the system may be programmed so that the compression member 38 cycles between maximum and latch suction levels without the compression member 36 closing during a point in each cycle, with the compression member 36 closing when the latch vacuum is exceeded.

Upon commencing milk extraction, the compression member 36 and compression member 38 can function in the same manner as in latching, but in a manner that follows an extraction waveform determined by the selected extraction pumping determined in real time by system controls which are responsive to the load cell assembly or pressure sensing assembly. At this stage, any sounds created by the pumping action of the system are decreased as milk or fluid flows through the pump mechanism. During the compression stroke of compression member 38, compression member 36 closes when the latch pressure/suction level is achieved. Continued compression by the compression member 38 increases the pressure in the tubing 32 downstream of the compression member 36 to establish a positive pressure to drive the contents (milk) of tube portion 32L out of the tube portion 32L through smaller tubing portion 32S2 downstream of 32L and out through a one-way valve. The positive pressure attained is sufficient to open the one-way valve for delivery of the milk out of the tubing 32 and into a milk collection container. In one embodiment, the positive pressure is in the range of 20 mm Hg to 40 mm Hg, typically about 25 mm Hg. Upon reversing the motion of compression member 38, compression member 36 opens when the suction level returns to the latch suction level and compression member 38 continues to open to increase the suction level to the maximum suction level.

The present disclosure can establish a latch vacuum to cause the flange or skin contact member/breast 14 to seal to the breast. The latch vacuum established by the system is currently about 60 mmHg, but can be any value in a range of from about 20 mmHg to about 100 mmHg. Once the system 10 has been latched to the breast via skin contact member 14, the system then cycles between the latch vacuum and a target (also referred to as "peak" or "maximum") suction level. Due to the fact that the system 10 does not cycle down to 0 mmHg, but maintains suction applied to the breast, with the minimum end of the suction cycle being the latch suction level (e.g., about 60 mm Hg), the nipple does not contract as much as it would with use of a prior art breast pump system. It has been observed that the nipple draws into the skin attachment member 10 with the initial latch achievement in an analogous fashion as the formation of a teat during breastfeeding. Once the vacuum cycles between the latch and target vacuum levels, there is significantly less motion of the nipple back and forth with the vacuum changes, as compared to what occurs with use of prior art systems. The nipple motion (distance between fully extended and fully retracted) during use of the present system is typically less than about 2 mm, and in some cases less than about 1 mm. Accordingly, the system provides latching that is not only more like natural nursing, but the reduced nipple motion is also more like natural nursing as evidenced by scientific literature. In one particular approach, the system can employ ultrasound to observe nipple motion during pumping to ensure that desired nipple motion is achieved.

This greatly reduced motion of the nipple during cycling results from establishment of the latch at latch vacuum level, and then limiting the range of vacuum swing between latch vacuum (suction) and peak vacuum (suction). Typically the difference in vacuum between latch vacuum and peak vacuum is less than 200 mmHg, more typically less than 150 mmHg. In one example, the latch vacuum was 50 mmHg and the peak vacuum was 200 mmHg, resulting in a vacuum difference of 150 mmHg.

Limiting the nipple motion as described with use of the present system offers several benefits to the user. One benefit is that there is less friction on the side of the nipple against the flange wall, thereby greatly reducing the risk of irritation, skin damage, pain, swelling, etc. As a result, the present system is significantly more comfortable to use by a nursing mother, and this benefit is increasingly noticeable over repeated uses. By maintaining at least a latch suction level at all times, the present system provides a more secure and persistent seal to the breast and significantly reduces the potential for leaks of air and/or milk. Because the nipple moves significantly less, this provides a more "natural" feel to the user that more closely simulates the feel of a nursing baby. Because the nipple travels less, this allows for the skin attachment member/flange 14 to be designed as a lower profile component, as its length can be shorter since it does not need to accommodate the greater length in nipple movement experienced by prior art systems. This allows the overall amount of protrusion of the system 10 from the breast to less than that in the prior art, as the overall length of the system is reduced by the reduction in length of the skin contact member/flange 14. Thus, the distance from the tip of nipple to exposed end of the housing the system is reduced.

The breast contact portion can be symmetrical about the nipple receiving portion although, alternatively, the nipple receiving portion could be offset. The skin contact member 14 is designed to reduce the internal volume of the nipple receiving portion, which is enabled by the significantly reduced amount of motion experienced by the nipple during a milk extraction process using a system 10 including skin contact member 14, according to the present disclosure. The nipple receiving portion of the skin contact member 14 is contoured to more closely match the natural shape of the nipple, thereby eliminating or significantly reducing dead space that exists around the nipple in prior art systems. The nipple receiving portion can be cylindrical in the portion adjoining the breast contact portion, and then can taper conically. This design allows for receiving a portion of the areola into the nipple receiving portion while also limiting dead space. The diameters of all cross-sections of the nipple receiving portion are contemplated to be large enough to allow nipple dilation. The length of the nipple receiving portion can be about 23 mm and the length may vary within a range of about 22 mm to about 29 mm. The length of the nipple receiving portion is sufficient to allow engorgement of the nipple under vacuum, without the distal tip of the nipple contacting the proximal end of the nipple receiving portion. In an alternative approach, the nipple receiving portion can be sized and/or shaped to mimic the anatomy of a child that is nursing. In this regard, rather than being generally cylindrical, the nipple receiving portion define more of a natural mouth shape or a generally rectangular sleeve with rounded corners and curved surfaces. The teat of the breast is thus formed into a more natural nursing shape by the natural shaped nipple receiving portion.

The internal contour 120 of the flange 14 is designed for use with the present system 10 and to maximize comfort of the user. The internal angles and generally flat portions also facilitate the ability to restrict portions of the breast from moving forward too much into the nipple receiving portion. The wider angle helps to prevent the breast tissue from being funneled into the nipple receiving portion, so that less breast tissue is received in the nipple receiving portion, making use of the flange 14 more comfortable than flanges of the prior art and providing space for nipple engorgement. By providing the wider angles, this also allows the overall system to be effectively shortened and allows the system to lie flatter against the breast to improve both comfort and appearance.

In one embodiment, the total system volume is about 24.0 cc. The total volume is calculated as the space in the nipple receiving portion (that is not occupied by the nipple) and tube portions 32S, 32L and 32S2 up to the milk collection or container assembly. In the embodiment with total system volume of about 24.0 cc, the active pump volume, i.e., the volume displacement achievable by compressing tube portion 32L from fully uncompressed to the limit of compression by compression member 38 is about 3.4 cc. When there is only air in the tubing 32 of the system 10, pressure swing by moving the compression member 38 inwardly against the tubing portion 32L and outwardly away from the tubing portion is limited, due to the compressibility of the air. In this embodiment, with the system under vacuum of −60 mmHg, a full stroke of the compression member (from compressed to fully uncompressed tube portion 32L) increases the vacuum to −160 mmHg. The ratio of pumping volume to total system volume can be important with regard to power and size of the pumping system. In this embodiment, the tube portion 32L was made of silicone. It has been recognized that reduced motion of the compression members when pumping allows for more quiet action of the pump motor, and a more quiet system overall. Further, the present system employs the milk expressed as the medium for system hydraulics, and this medium is in direct contact with the user's breast against which a vacuum is drawn. Thus, the system can employ air suction against the breast for initial latching and pumping and then converts to utilize expressed breast milk for pumping action or power.

During let down operation, the system 10 operates to effect let down of the milk in the breast, prior to extraction, with a maximum suction target of up to 120 mmHg (typically, about 100 mmHg (−100 mmHg pressure)) to establish let down. The goal of letdown (or non-nutritive suction) is to stimulate the breast to express milk. The relatively shallow (small vacuum change range) and relatively fast frequency of the pumping during this phase are meant to mimic the initial suckling action of a child at the breast. This is because during let down phase, the suction pressure is not allowed to exceed the maximum let down suction of 110 mmHg or 120 mmHg, or whatever the maximum let down suction is set at. Therefore, as the compression member 38 is drawn in a direction away from the tube portion 32L, the system 10 is designed to reach −100 mmHg (a suction pressure of 100 mmHg) (or −120 mmHg, or whatever the maximum let down suction is designed to be), by the time that the compression member 38 has reached a position in which tube 32L is mostly uncompressed.

During let down (non-nutritive) the system software and/ or firmware communicates instructions to system motors based upon readings taken and communicated from the pressure sensing assembly so that the system is configured to operate between −60 mmHg and −100 mmHg in one example. In this example, the compression member 38 can compress the tubing portion 32L nearly fully and then be moved away from the tubing portion 32L to generate vacuum. The maximum latch suction pressure of −100 mmHg will be reached with a small amount of rebound of the tubing portion 32L and the compression member 38 can be cycled relative to the tubing portion 32L between −100 mmHg and −60 mmHg in a narrow range or band near full compression of the tube portion 32L. As milk flows, that narrow band shifts at which point the tube portion 32L will be purged by fully compressing it to drive out the contents and thereby regain more capacity for pumping with relatively less compression of the tube portion 32L again.

The system 10 is responsive to pressure changes within the tubing 32 caused by entry of milk into the tubing 32. Referring again to FIG. 7, the compression elements 36 and 38 are operatively connected to a driver 44, 46, respectively, for independent, but coordinated driving and retraction of the compression elements 36, 38. When electrically-powered drivers are used, a battery 48 is electrically connected to the drivers 44, 46, as well as the controller 52 and pressure sensor 54, and supplies the power necessary to operate the drivers 44, 46 to drive the compression and retraction of the compression elements 36, 38.

The sensor 54 is used to provide feedback to the controller 52 for controlling the pumping cycles to achieve and/or maintain desired vacuum levels. Sensor 54 is preferred to be a load cell sensor providing data utilized to calculate system pressure, but could also be a pressure, flow, temperature, proximity, motion sensor or other sensor capable of providing information usable to monitor the safety or function of the pump mechanism of system 10. As shown, sensor 54 is a non-contact sensor 54, meaning that it is not in fluid communication with the milk or vacuum space of the system 10.

As described above, the conduit or flex-tube 32 is placed in operative connection with a motor. An opposite side of the flex-tube 32 is equipped with the sensor 54 that takes the form of a load cell. The positioning of the motor is tracked and the force on the tube 34 is assessed to determine internal vacuum. By employing machine learning or supervised learning regression techniques, the system 10 can be trained to interpret the motor positioning and tubing strain (as well as motor speed or pump settings), while compensating for noise and hysteresis, to arrive at a pressure/vacuum level. More specifically, a neural net system or any mathematical regression of the data can be incorporated into system firmware so that sensor input can be translated to pressure/vacuum levels. In this regard, the system 10 can include or communicate with a non-transitory computer readable medium having stored thereon instructions executable by a computing device of the system or external to the system to cause the computing devices to perform functions associated with and directed by the firmware.

To train the neural net, large amount of data is generated, both from an accurate vacuum reading as well as strain gauge readings. All of the data is sent to software so that post processing can be conducted. It has been determined that data taken during normal pump flow lends itself best to training the system 10. For example, data can be gathered when flow is at 2-3 ml/min, and when system pumping is slow at each pressure target. This approach ensures that the motor moves along its entire travel cycle relatively evenly and noise associated with high flow is not introduced into calculations. Highly controlled settings are also used to generate data so that unbiased data is generated. Further, system accuracy can be increased when using specifically generated neural nets for specific ranges of pressures. A special code is employed to isolate data from different pumping limits in training data, and uses only that data to generate a neural net that is used later when pumping to the same limits.

Figure 8:
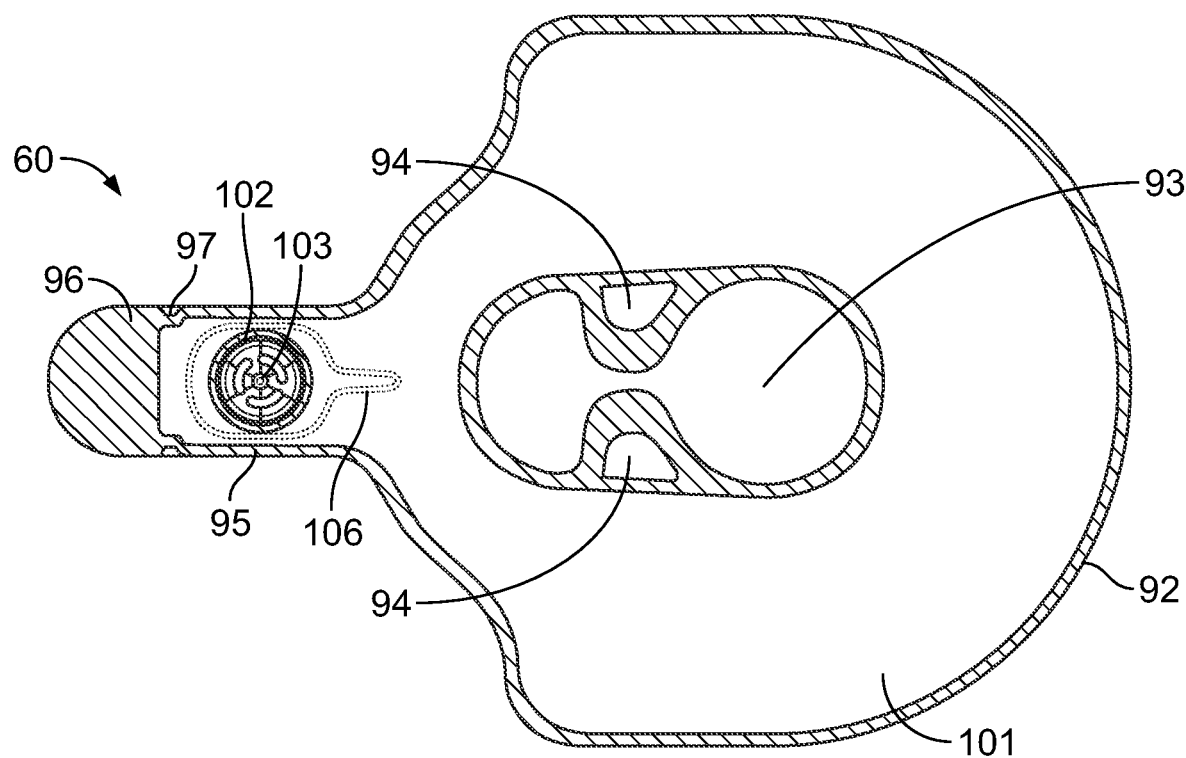
FIG. 8 is a top view, depicting one embodiment of a storage collection assembly of the present disclosure.
Figure 9:
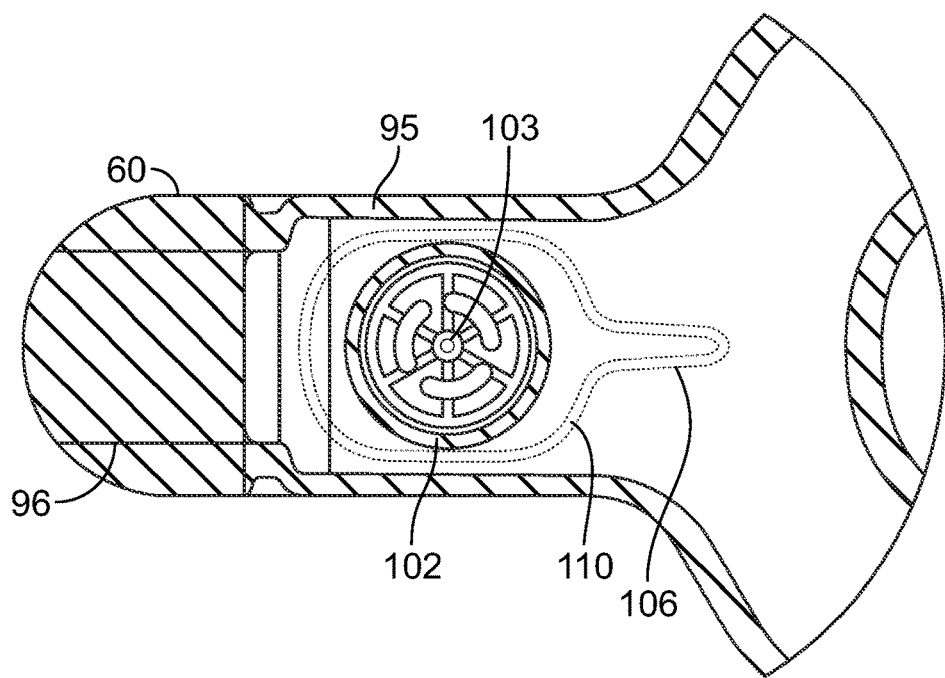
FIG. 9 is an enlarged view, depicting a neck and valve of the storage collection assembly of FIG. 8.
Figure 10:
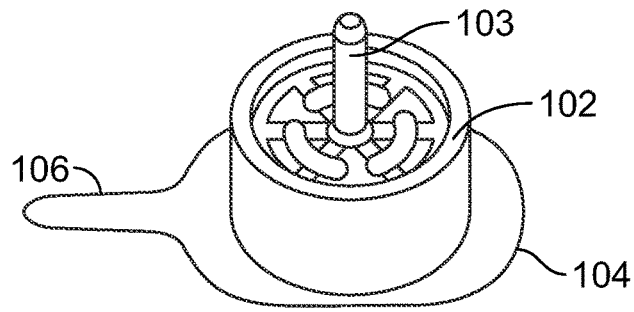
FIG. 10 is an enlarged view, depicting a valve assembly of the storage collection assembly.

Turning now to FIGS. 8-10, one embodiment of a collection or container assembly 60 is shown. In one particular embodiment, the collection or container assembly 60 can be formed from two 2.5-3.0 mil sheets of material that can be band welded or otherwise joined together along a perimeter 92 of the assembly, and can be sized to retain up to 4.5 ounces, or alternatively 8 ounces of fluid. In particular, the collection or container assembly 60 can be pre-formed to optimize or maximize the space inside the pump system and flange. For shipping, the collection or container assembly can be pulled closed with a vacuum to make it flat or thin for packaging or handling. A body of the collection or container assembly is generally bladder shaped and includes a generally asymmetrical oval central opening 93 created by an interior band seal. In one particular approach, the body can additionally include gussets to provide more volume. A pair of wings 94 extend into the central opening 93 and are provided for handling and facilitating positioning of the collection or container assembly 60 within a pump system 10. A narrow neck portion 95 is centrally positioned and extends longitudinally away from the central opening 93. The neck portion 95 includes a tab portion 96 that provides structure for grasping and removal, and can further include one or more cut-outs or tear-able elements 97 provided for aiding in tearing the container 90. Further scoring is also contemplated to help in the tearing of the bag assembly 90. Also, in alternative embodiments, the collection or container assembly 90 can be re-sealable, re-usable, include larger or smaller openings or include spout structure for pouring contents. A spout can also be attached to the fitment or valve of the collection assembly to facilitate pouring. Such a spout could further include structure which temporarily or permanently defeats the valve or fitment. The valve of the collection or container assembly can also be re-usable with a second or subsequent collection or container assembly, and therefore is removable from the container assembly.

Moreover, in one particular embodiment, the collection or container assembly 90 can be made from polyethylene and can be bisphenol A free, as well as food grade material. It should be freezable without tearing and withstand approximately 0-80 degree Celsius temperatures. Additionally, tensile strength can be from 2300-2900 psi and tear strength from 440-600 psi, with a water vapor transmission rate max of about 0.5 g/100 in$^2$/24 hrs and an oxygen transfer rate of about 150 cc/100 in$^2$/24 hrs. In alternate embodiments, the material of the collection or container assembly can be Gore-tex or Tyvek, for example. Such alternative materials can permit out-gassing. Accordingly, a non-closed or unsealed system is also contemplated. In this specific regard, other vents or approaches to venting the system can be incorporated into one or more embodiments. Thus, self-venting of the container assembly or active venting while using the pump system or after use can be accommodated. In one approach, a pressure valve can be incorporated into the system and configured to activate after some system pressure is reached, and further the valve can be designed to act as a fluid barrier, only allowing air and not fluid to escape.

It is contemplated that the system is configured to pump into a sealed collection or container assembly 60, or one that incudes an integral valve or an otherwise airtight collection or container assembly 60, or combinations thereof. In this specific regard, the system can alternatively or additionally be closed and never vented to the atmosphere, and/or the system suction is only reduced through the flow of milk into the system. Thus, in at least one approach, milk or fluid that is pumped through the system is never exposed to new outside air from the environment once it enters the collection or container assembly. Accordingly, the orientation of the pump system or person has virtually no impact on the functioning of the system (i.e., no spills). The collection or container assembly can include a rigid or flexible sealing component, such as a ring or gasket into which the pump or container valve is pushed or twisted and sealed. The collection or container assembly can also include an opening or hole or structure that is pierced such that the container assembly seals about the member that goes into it. Moreover, there are contemplated a range of disposable and durable combinations of container 101 and valve fitment 102 arrangements such that one or both of the container bag 101 and fitment 102 are disposable or reusable. Additionally, the container can configured to be inside or outside of the pump housing.

Figure 11A:
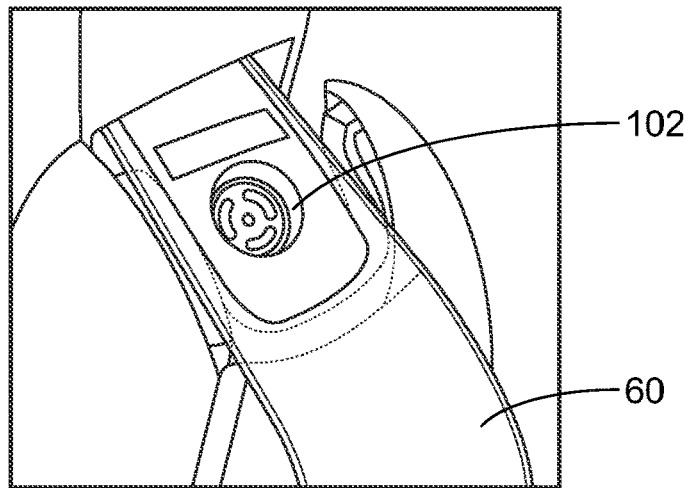
FIG. 11A is a perspective view, depicting a storage collection assembly connected to the system.
Figure 11B:
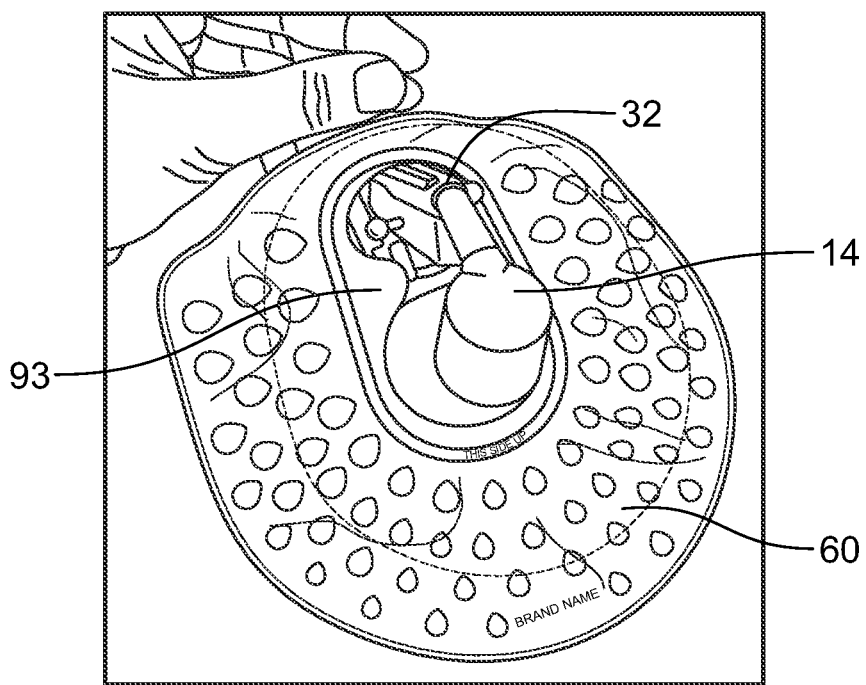
FIG. 11B is a perspective view, depicting a first step in installing a collection assembly.
Figure 11C:
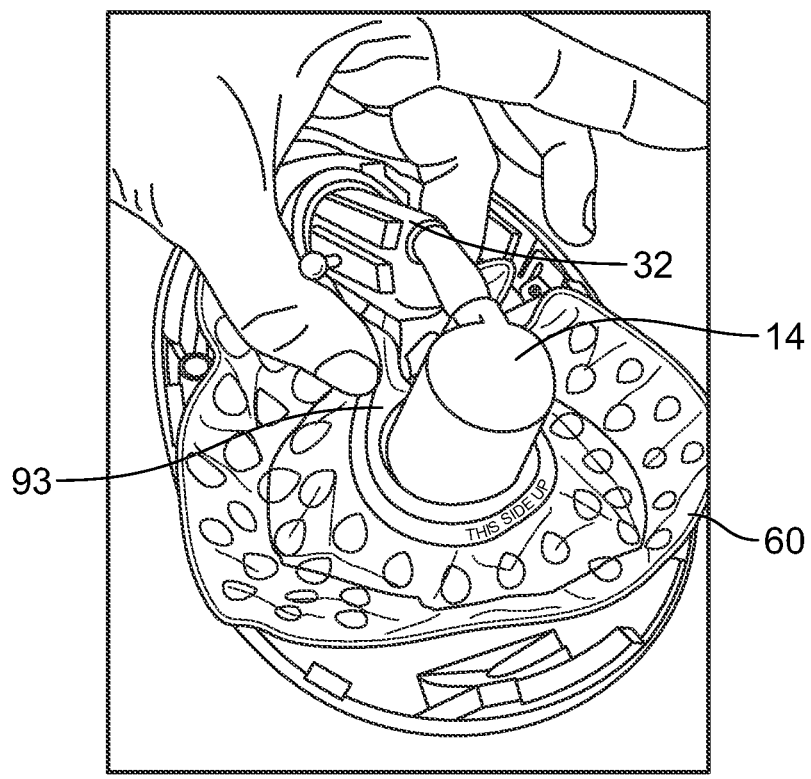
FIG. 11C is a perspective view, depicting a second step in installing a collection assembly.
Figure 11D:
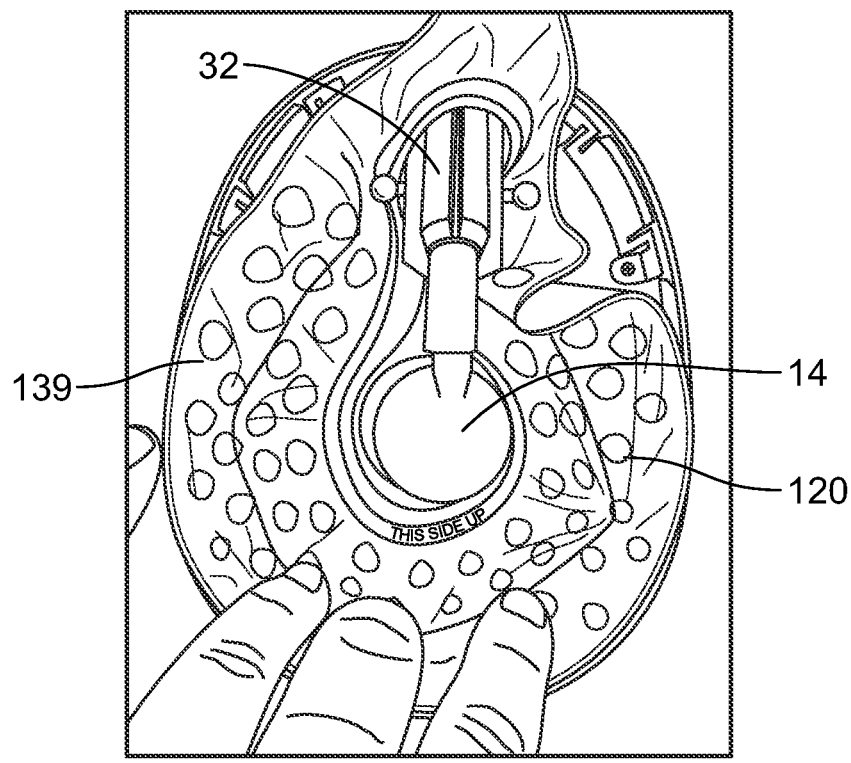
FIG. 11D is a top view, depicting a third installation step.
Figure 11E:
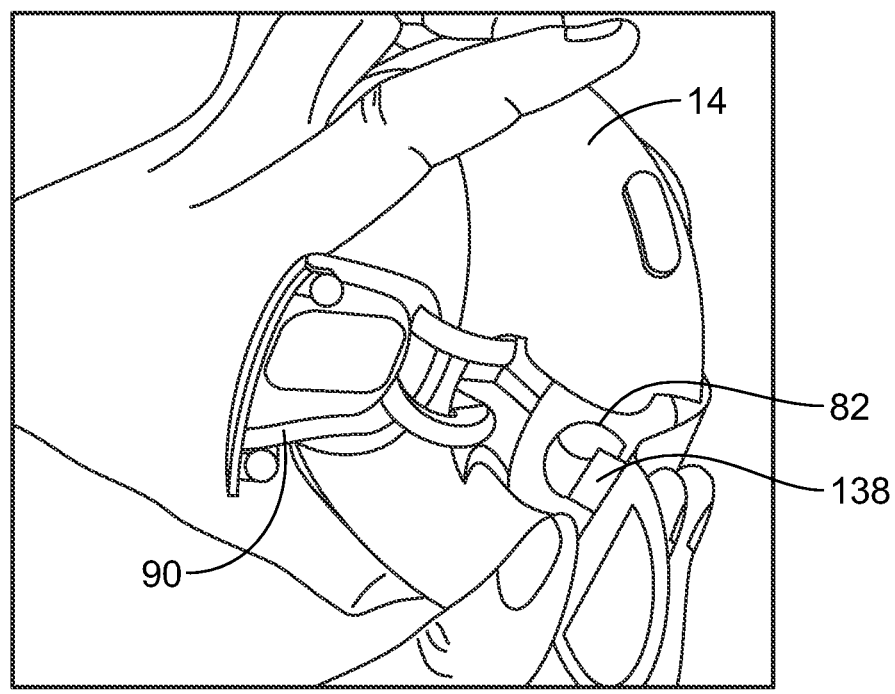
FIG. 11E shows yet another collection assembly installation step.

The fitment 102 can embody a valve such as an umbrella valve assembly 103 or other type of one-way valve connected in fluid communication with the storage container 101. The fitment can also assume a myriad of alternative embodiments, and can additionally or alternatively be formed integral with the container. For example, in one contemplated approach, the fitment and/or the valve can be formed as part of the container rather than define a separate component attached to the container. As shown in FIGS. 8-10, however, the tail 104 of the umbrella valve 103 can be employed to defeat the valve when desired such as to remove gases, by turning it and engaging the tail against the valve body. Additionally, the valve includes a generally cylindrical portion having a diameter of approximately 0.585 inches extending from a flat base 104 having a width of approximately 0.875 inches. It is the flat base portion 104 that is captured and sealed between the two sheets of bag container material and includes a tail 106. The tail 106 functions to ensure flow through the neck portion of the container assembly 60 particularly when it is placed into the pump assembly (See FIG. 11A), and has a narrow, elongated shape that permits flow thereabout. That is, the tail 106 maintains flow through the neck even when the neck is folded as the container assembly is attached to the breast pump body. Valve 103 prevents back flow of milk into the flex-tube 32, and facilitates maintaining the suction (vacuum) level in the flex-tube 32. In other embodiments, other features can be provided or built into a valve to allow for depression or otherwise overcome the valve to vent air. Such approaches can involve a protrusion that is attached or associated with the valve so that as the protrusion is pushed toward the collection or container assembly, an edge of the valve is translated to thereby break the valve internal seal. Moreover, a nub can be attached to valve structure and configured inside the container assembly. Tugging on the nub through a layer of the container assembly thus results in freeing an edge of the valve and breaking the valve seal.

In at least one embodiment, the pressure at which the valve 103 opens to allow flow into the milk collection container 60 is about 25 mm Hg. The valve 103 can be configured and designed such that it allows fluid to flow through it when the pressure in conduit or flex tubing 32 is positive, e.g., about 25 mm Hg, or some other predesigned "crack pressure". The action of the compression elements cycles between increasing vacuum when the compression elements move in a direction away from flex-tube 32 and decreasing when the compression elements compress the flex-tube 32, but typically should not increase the vacuum to greater than the predetermined maximum vacuum. As the compression elements 36, 38 compress the flex-tube 32, the pressure in the system 10 goes up and reaches the minimum suction level (e.g., latch suction level, such as −60 mmHg, −30 mm Hg, or some other predetermined latch suction level), at which time the compression member (pinch valve) 36 seals off portion 32S thereby maintaining the minimum suction (latch suction) against the breast. Continued compression of portion 32L by compression member 38 continues to increase the pressure downstream of compression member 36, until the crack pressure is reached (e.g., 25 mm Hg or some other predetermined, positive crack pressure), that opens the valve 103. The compression elements 36, 38 continue compressing flex-tube 32, pumping fluid (milk) through the valve 103 and into the collection container assembly 60 until the compression element 38 reaches an end point in travel. The end point in travel of the compression element 38 against portion 32L may be predetermined, or may be calculated in real time by the controller 52 using feedback from pressure sensor 54 and feedback from the driver of the compression element 38, from which the controller 52 can calculate the relative position of the compression element 38 over the course of its travel. The compression member 36 remains closed throughout this process, as it is used to seal off the tube 32 the entire time that the compression element 38 is pumping milk out into the collection container assembly 60. As the compression elements 36, 38 reverse direction and pull away from the flex-tube 32, they start the cycle again.

As milk enters the system, the suction level decreases (pressure increases). The feedback provided by pressure monitoring via pressure sensor 54 provides input to a feedback loop that adjusts the position of the compression member 38 to maintain the desired vacuum (pressure) within the conduit or flex tubing 32 by compensating for the changes in pressure that occur to changing amounts of milk in the flex tubing 32. For example, for a relatively larger amount of milk in the tubing, this will require a relatively shorter stroke of the compression member 38 to achieve the latch pressure. This modification can be addressed by either slowing the movements of the compression member 38 to achieve the same timing cycle for pumping, or increasing the cycle frequency due to the less time taken for the shorter strokes of the compression member 38.

Use of a system 10 provided with a non-contact pressure sensor 54 would include loading the collection or container assembly 60 into the system 10 (See FIGS. 11A-E). In a first step (FIG. 11B), the flange 14 is removed from engagement with the remainder of the system 10. Attached to the flange is the conduit or flex-tube 32. The central opening 93 is placed over a central projection of the flange 14 and the flex-tube 32. Next, the user can pinch the wings 94 under the flex-tube 32 (FIG. 11C) followed by tucking the collection or container assembly 60 into the flange 14. The fitment 102 is placed within the collar 82 of the flex-tube 32 (See FIGS. 11A and 11E). In certain embodiments, the collection or container assembly 60 can have useful labels, icons or notifications. For example, milk droplet icons can be printed on the collection or container assembly 60 in increasing size to indicate the degree to which the container is filled, and a "this side up" message can be included to aid the user in properly installing collection or container assembly 60. Also, the container assembly 60 includes a number of surfaces away from storage areas where printing or handwriting can be placed. For example, the wings 94 can be used as a writing or printing surface as can the pull tab 96. Similar labeling or messages (for example, a "thanks mom" message) can be included on the collar 84 or other portion of the flex-tube 32 to aid in properly orienting the flex-tube with respect to the flange 14. It is to be recognized that the collection or container assembly can be placed in alternative locations as well. For example, the collection or container assembly can be configured around the nipple of the breast. In this regard, the container assembly itself can form the desired flange or breast contacting structure into its core construction. In one specific approach, the container assembly can also include more surface area facing the breast superior to the nipple than inferior thereto.

It is contemplated that the door assembly 90 be employed to both provide a continuous contour of the flange 14 for engaging a user's breast as well as to support the engagement of the collection or container assembly 60 with the system 10. Thus, the door assembly 90 can be configured to pivot with respect to the flange 14, and employed to close the system 10 as it is snapped over and closes the pump. With this approach, the fitment 102 and container bag 101 are securely sandwiched between the collar 82 of the conduit or flex-tube 32 and the door assembly 90, with a cylindrical portion of the fitment 102 received within the collar 82. The collar 82 can also provide rigidity to the flex-tube 32 so that it can be loaded into the flange 14 as well as to provide an annular back-up when the fitment 102 is inserted. Ribs or o-rings can be provided on an interior surface of the flex-tube to facilitate sealing with the fitment 102 and can have a radius of approximately 0.64 mm. In one embodiment, the interior diameter of the flex-tube between the ribs can be approximately 14.6+/−0.17 mm, while the outer diameter of the fitment 102 can be on the order of 14.8+/−0.17 mm so that an interference fit results, with a force of around 1-2.5 lbs.

Figure 12:
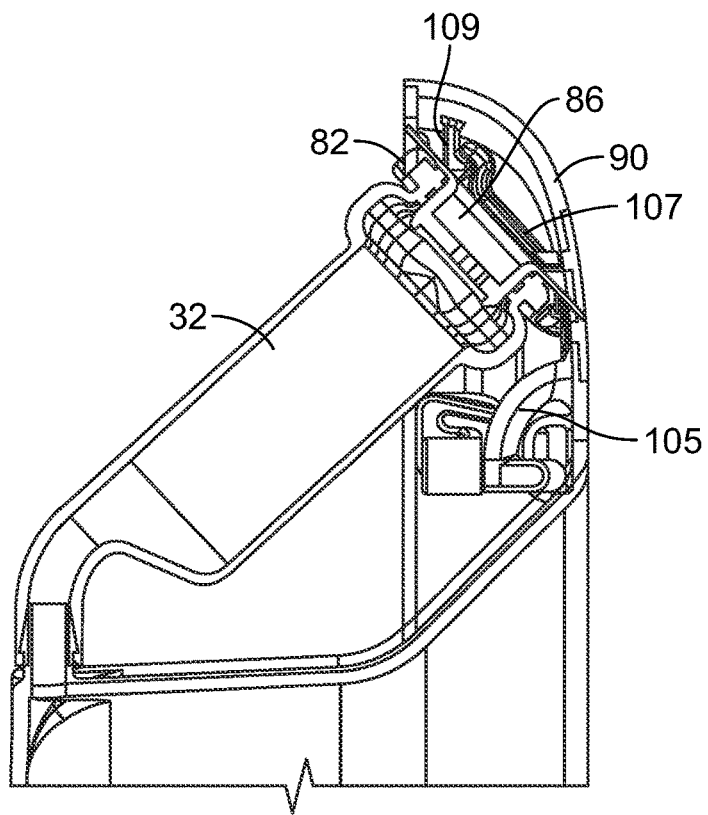
FIG. 12 is a cross-sectional view, depicting a portion of the system.
Figure 13:
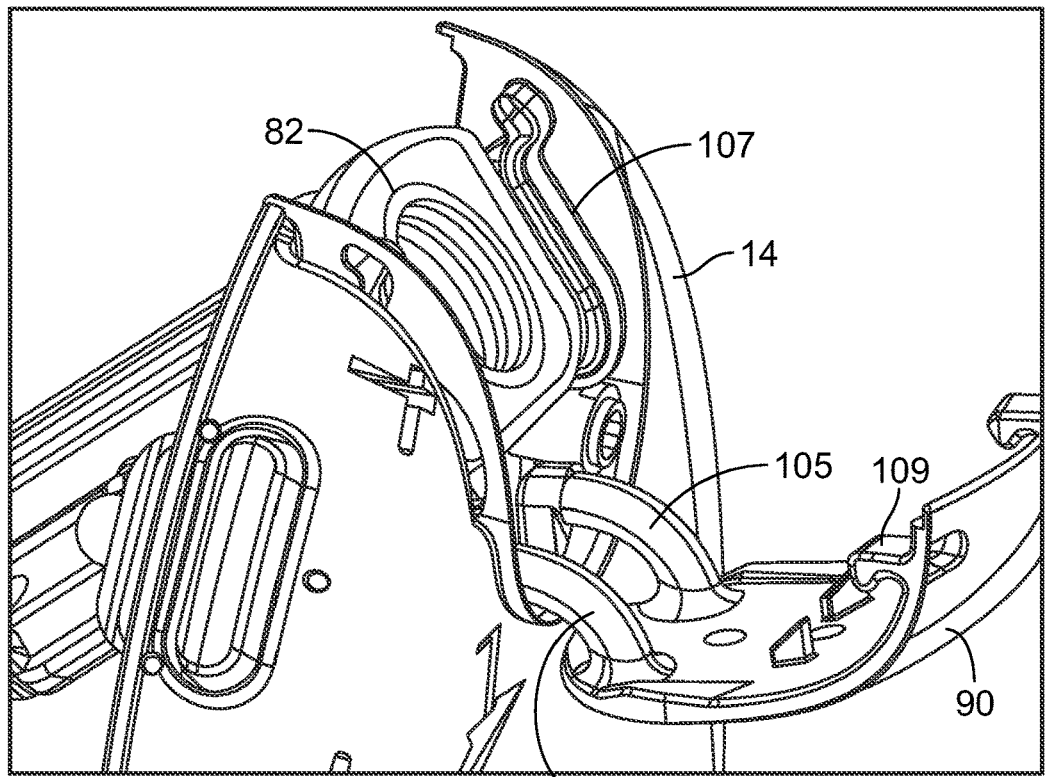
FIG. 13 is a perspective view, depicting a door assembly of the system.
Figure 14:
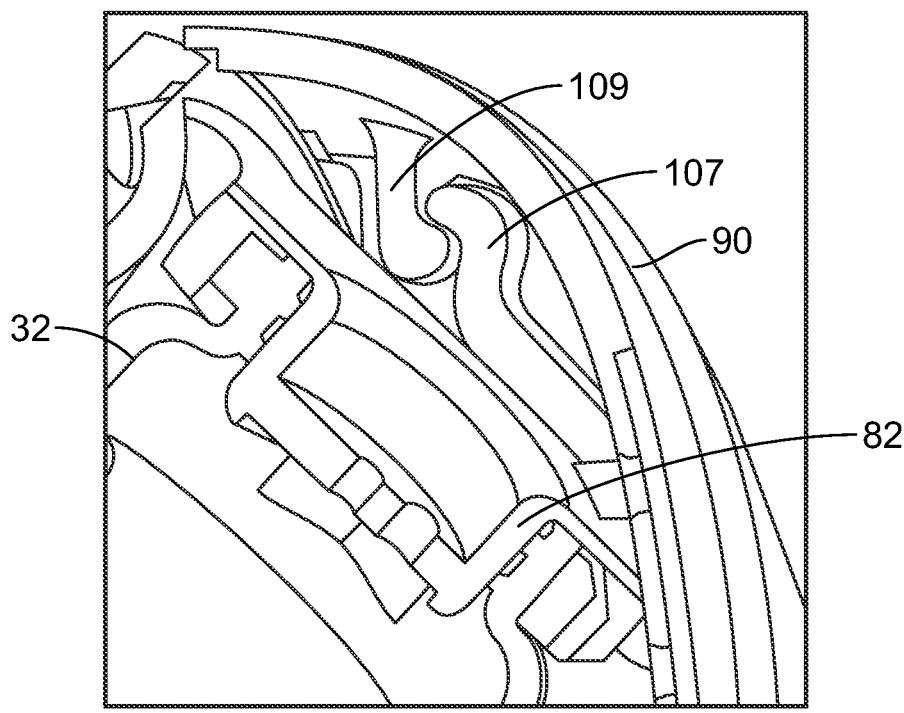
FIG. 14 is a cross-sectional view, depicting details of the door assembly.
Figure 15:
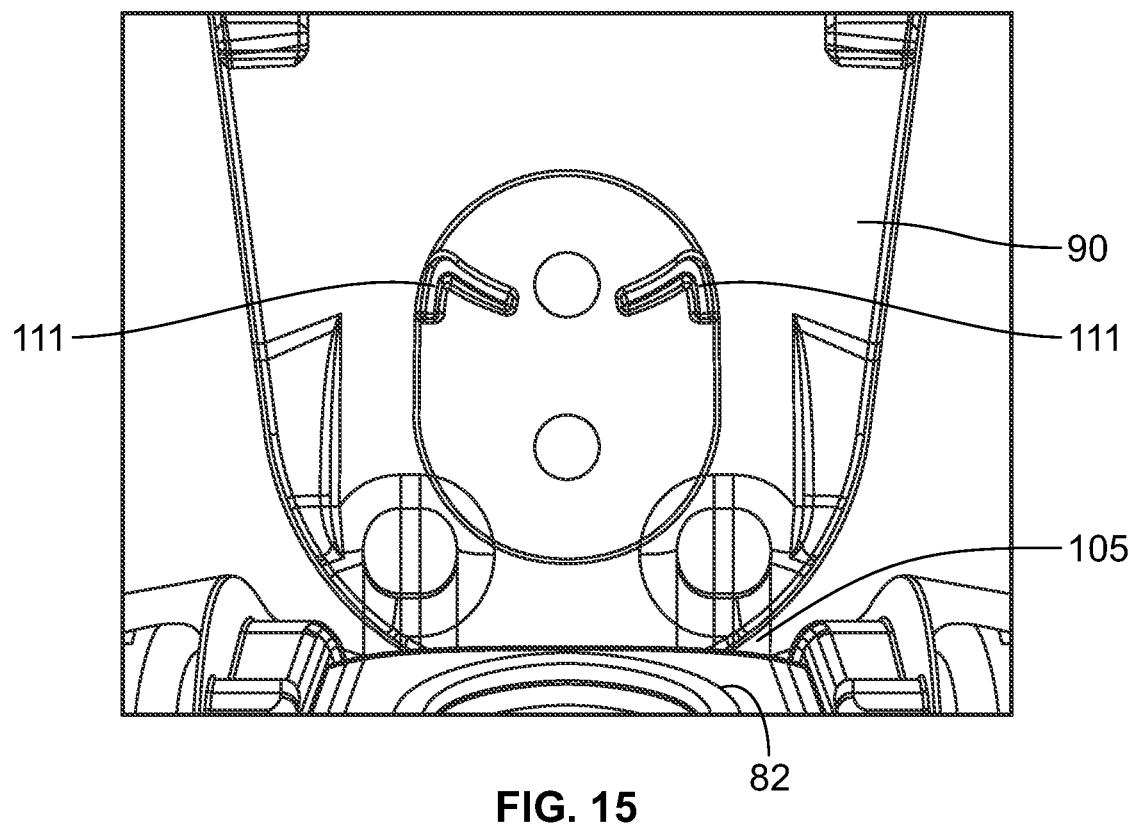
FIG. 15 shows details of the door assembly.

As best seen in FIGS. 12 and 13, the door assembly 90 further includes a pair of spaced and curved guiding arms 105. The arms 105 are contoured to guide the door assembly 90 as it closes over and about a pair of curved railings 107. In this way, as the door assembly 90 rotates toward the conduit or flex-tube 32, a latch 109 of the door assembly 90 first clears and then seats beyond and behind the railings 107 to thereby provide a robust engagement with the flange 14 and bag assembly 60 when it is loaded in the system 10 (See also FIG. 11). As best seen in FIGS. 8 and 9, the fitment 102 includes a scalloped portion 110 which functions to facilitate this robust engagement and provide relief of undue stresses being placed upon the bag assembly when securely mounted within the system by resisting kinking. The door assembly can further include one or more ribs 111 (FIG. 15) that engage and provide directed support to the fitment 102.

Figure 16:
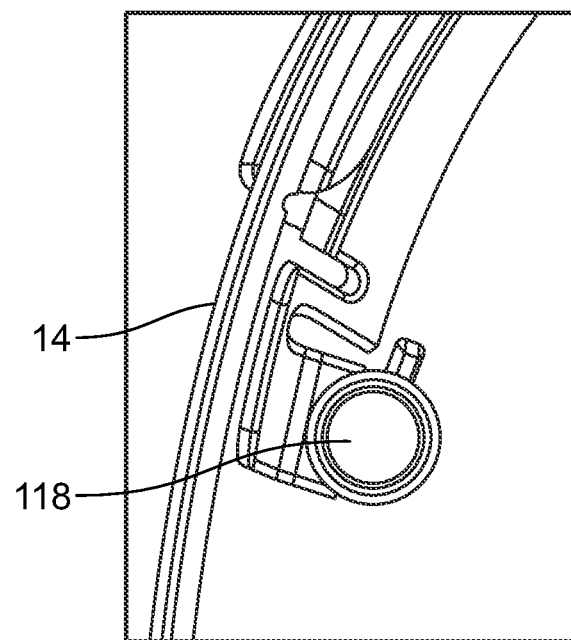
FIG. 16 is an enlarged view, depicting structure of a pinch protection assembly.
Figure 17:
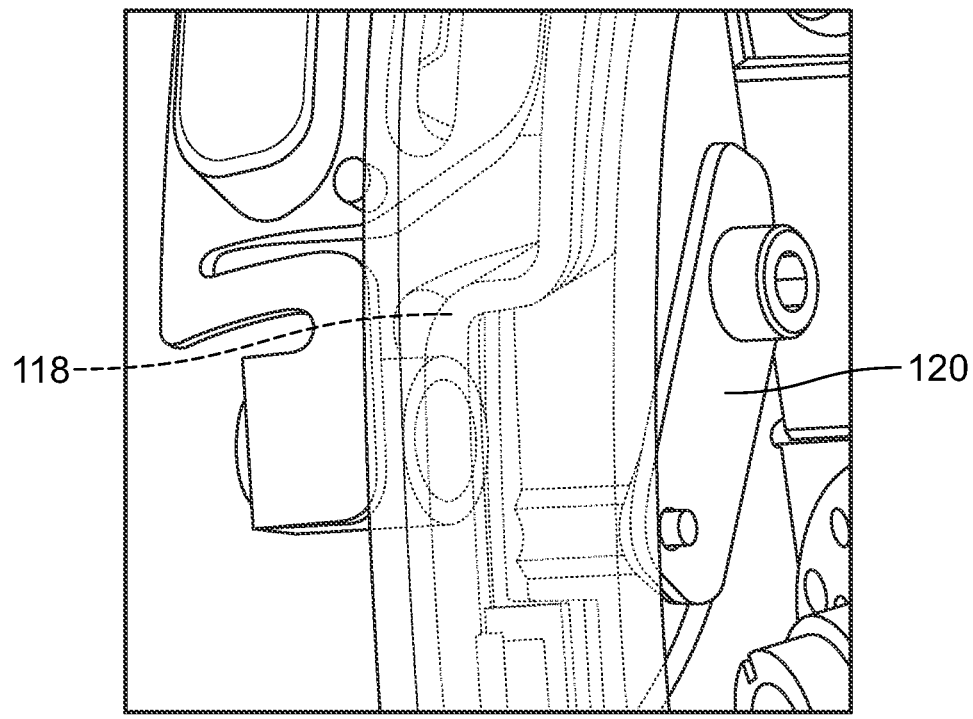
FIG. 17 is an enlarged view, depicting other structure of a pinch protection assembly.
Figure 18:
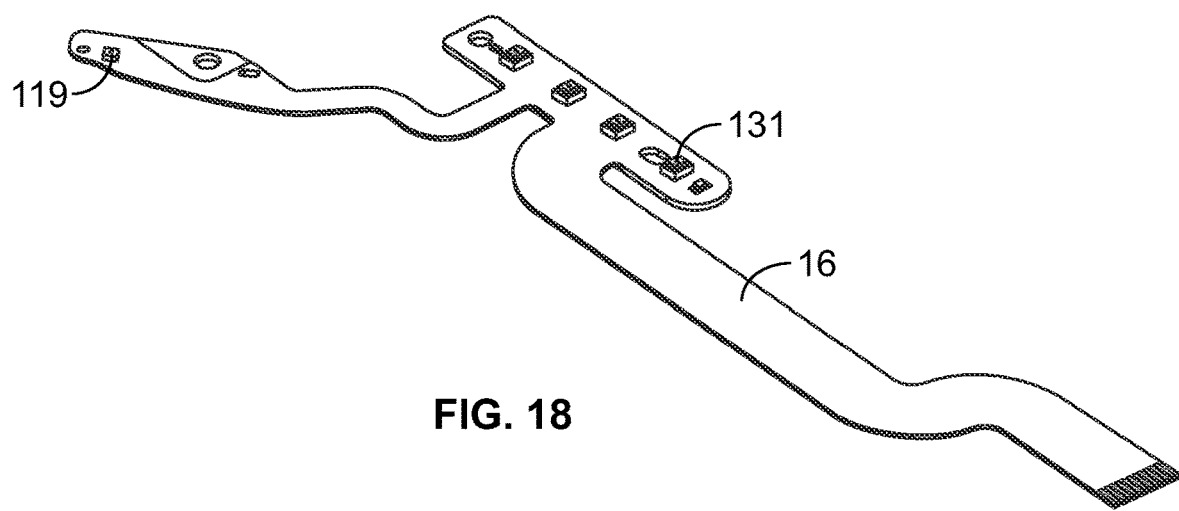
FIG. 18 is a perspective view, depicting a flex circuit of the system.

Turning now to FIGS. 16-18, there is shown an approach to protecting against pinching by moveable parts of the pump system 10. One or more magnets 118 can be attached to the flange 14. A corresponding sensor 119 (such as a hall effect sensor) can be attached to the flex circuit 16 that is mounted to a mounting bracket 120 (See also FIG. 3). The system 10 can be configured to only permit the motor to be activated when the sensor detects the magnet 118. In this way, the pumping action of the system and in particular, the compression members will not move until the flange 14 is attached properly to the housing 12, consequently avoiding any pinching or engagement of such components with the user. In other approaches, mechanical or electronic switches or RFID technology, or optical sensor or sonar technology can be incorporated into the system to provide the desired safeguards, such that the system will not operate unless all components of the system (i.e., flange, tubing and storage) are fully connected.

In another approach, the system 10 can include firmware that operates to track system pressure on a load cell. Here, the motor paddle can be arranged and controlled by firmware so that it is moved outwardly 0.5 mm or some defined distance and pressure on the load cell is observed to see if the conduit or flex-tube is properly installed. Where the pressure observed is not as expected, such as if there is no pressure, the motors will not be permitted to move inward for pumping. Using a similar technique, proper collection container install can be tested. After the motor extends, the pinch can seal the flex-tube. Once the motor comes back out, a vacuum will only be measured if the bag is properly installed, sealing air from filling the tube on the container side.

It has also been recognized that fluid ingress protection may be necessary for the pump system. Thus, it is contemplated that various gaskets can be configured within the structure of the system. One particular location for a gasket is the interface between the chassis and housing, and accordingly, a specially designed gasket is configured about a perimeter of the chassis along a section which is intended to engage the housing. In this regard, a 0.3 mm interference fit is contemplated between the gasket and the housing. Also, gaskets can be configured about moving receiver structure such as that of the load cell and motor to help prevent fluid ingress.

Figures 19, 20:
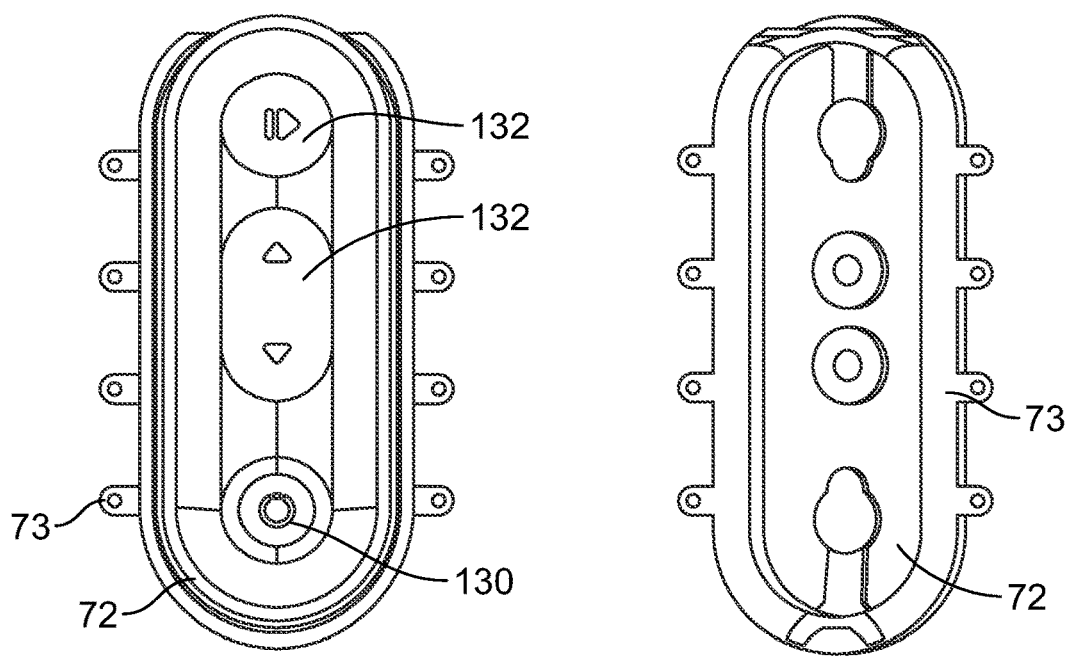
FIG. 19 is a top view, depicting a user interface assembly.
FIG. 20 is a bottom view, depicting further details of the user interface assembly.
Figure 21:
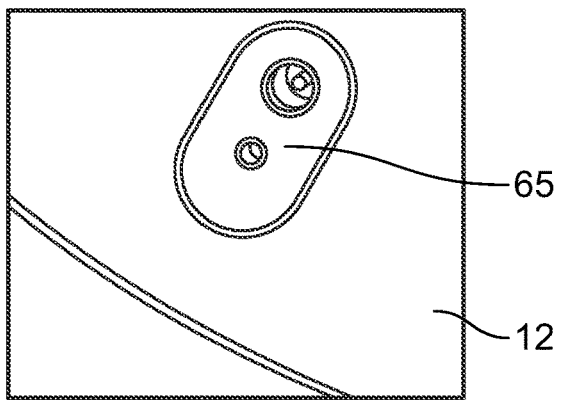
FIG. 21 shows power access support structure of the system.

Once the flange or skin contact member 14 is placed onto the main body/pump housing 34 then pump power can be engaged. Referring now to FIGS. 19-20, there is shown an enlarged view of the user interface panel which as stated above includes a button membrane 72 and a button membrane housing 73 each supported on the housing 12 and placed in engagement with the flex-circuit that provides the user with system control. Here, the membrane 72 acts as a light pipe. Light emission, intensity and button deflection forces are configured for convenient and effective interaction by the user. Accordingly, pressing the power button 130 functions to start the pump system 10 through its interaction with a switch 131 configured on the flex circuit 16 (See FIG. 18). It is noted that other switches 132 can further be provided on the flex circuit which line up with other contemplated system control buttons included on the flex membrane 72. Should the system 10 require external power or the battery charged, access to supporting electronics is gained through the cover jack 65 that is configured in the shell 12 (FIG. 21).

As the pump system 10 goes through a power up routine, the controller 52 reads force on the load cell when a load cell is used as the pressure sensor 54. This is the load measured by the load cell, before the skin contact member 14 has been applied to the breast, so in one approach it is a state in which the pressure in the conduit or flex-tube 32 is atmospheric pressure. The controller 52 then calibrates the system such that the preload force or position or measured load or strain equates to atmospheric pressure. Based upon a neural network or computer learning, load or strain detected at the flex-tube 32 can be converted to pressure readings in the system 10 during operation of the breast pump system 10 upon attachment to the breast.

The system 10 can calculate the volume of milk pumped into system or alternatively the volume collected in the milk collection container assembly 60. By knowing the dimensions of the conduit or flex tubing 32 downstream of the compression member 36 when compression member 36 has sealed off tubing portion 32S, the overall volume capacity of the system 10 downstream of compression member 36 can be calculated. With reference again to FIG. 7, tracking of the position of the compression member 38 relative to the tube 32 (such as by knowing the driver 46 position at all times, for example), dictates the volume change in the tubing 32. As the pumping process is carried out, pumping/purging of milk into the milk collection container occurs when the compression member 36 has closed off the small tube portion 32S at the location of compression. When the compression member 36 has closed off tube portion 32S, the change in position of compression member 38 that occurs to carry out the purge of milk from the flex tubing 32 and into the milk collection container 60 is used to calculate the change in volume of the tubing 32 downstream of the compression member 36, which equates with volume of milk that is pushed into the milk collection container 60 bag.

In particular, under one algorithm, as flow enters the system 10, it is recognized that the motor must move further and further out to generate latch vacuum. Tracking this movement and the rate of position change of compression or paddle members as they generate latch vacuum is one way of measuring flow. The slope of a line that is associated with tracking paddle locations for latch vacuum, for example, is directly proportional to flow. After a tuning step to correlate this relationship, calculating flow from the slope of this line can be readily accomplished.

Using another approach, the number of purges can be tracked when the system is full for the purpose of measuring flow. As stated, it can be determined when the system 10 is purging fluid versus purging air since the forces are much higher for purging fluid than purging air. Thus, counting the number of purges that contain fluid, and knowing the volume that is purged for each purge leads to a calculation of flow without requiring significant system tuning or calibration, and avoiding confusing a slow air leak with flow. Leaks can also be detected by employing an algorithm involving closing the pinch compression member, followed by closing the pump compression or paddle member, and then pulling the pump compression member outwardly to create a vacuum. By then holding the pump compression member in this position and verifying the vacuum is maintained, it can be determined if there is a leak in the system 10.

In addition to calculating the volume of milk purged with each purge cycle, the system (via controller 52) can sum the volumes from all purge cycles to calculate the total volume entering the pump or alternatively pushed into the milk collection container 60 during a milk extraction session. This volume can be stored with a unique identifier provided to the milk container so that the system 10 keeps a record of how much milk is stored in each milk collection container 60. This information can also be time stamped so that the user will know the time and date that milk was collected, regarding each milk collection container. Additional statistics can be calculated, including, but not limited to: average volume per extraction session, total volume extracted for any given day, average milk extraction volume per day, etc. Any and all of this data can be exported to an external computer, either manually, or it may be automatically uploaded to the computer when the computer is within range of the system 10 for wireless communication, or when the computer is connected to the system by wire. Further optionally, any or all of this data can be either manually or automatically uploaded to a cloud service over the Internet, either wirelessly or by wire.

Figure 7B:
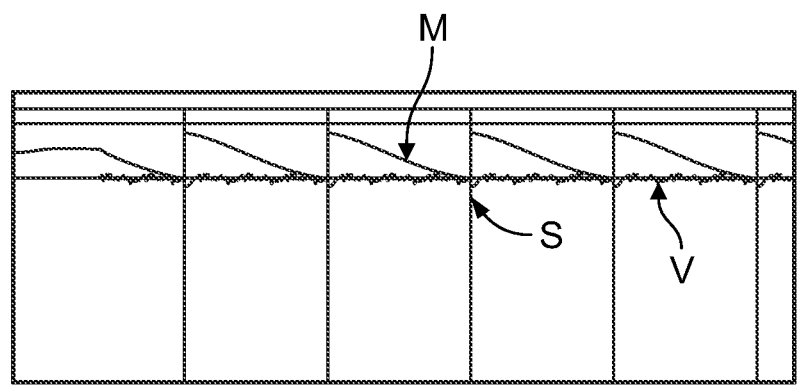
FIG. 7B is a graphical representation, depicting motor position and vacuum versus time.
Figure 7C:
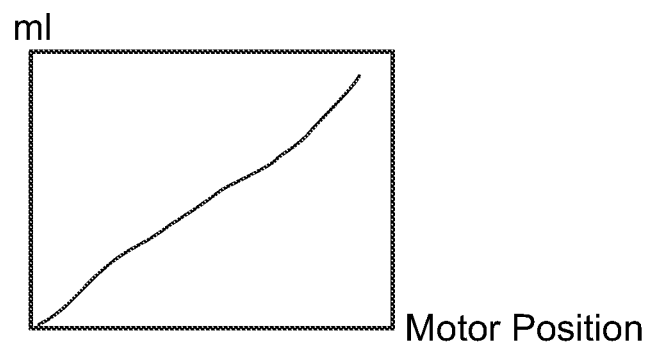
FIG. 7C is a graphical representation, depicting motor position versus volume.

In one preferred approach, volume that is extracted from a breast is calculated by building a map of motor location versus volume at a specific vacuum such as −60 mmHg, since the same is a reliable and predictably repeatable vacuum level. To build this relationship, various known rates of flow are created within the breast pump, and motor locations at −60 mmHg are identified and stored as data. A script is then employed to extract such data to build this motor versus volume scale. In particular, as shown in FIG. 7B line M represents motor location versus time and line V represents vacuum versus time. This data is entered into the script to arrive at a graph of volume over time. The script looks at indications of times of purge and tosses out data except a first clean start and finish of a cycle between purges represented by the spike S in FIG. 7B. An adjustment is made for time such that relative time for the data selected replaces absolute time. The script also functions to filter out data that is too far above or below −60 mmHg. Relative time is then turned into volume in that motor location becomes volume difference over a relative time span. This data can be plotted as a line (See FIG. 7C), the area under which represents volume. The output of the script represented as a line having a particular slope is expressed as numbers and as a $6^{th}$ order equation representing the line. This $6^{th}$ order equation is incorporated into the code base and is employed during real time to convert measured motor locations during pumping at approximately −60 mmHg into volume. Calculus is thus ultimately employed to arrive at this volume calculation in that motor location versus volume is integrated between two points to determine differences in volume. At certain levels of flow there can be an adjustment factor multiplied by volumes calculated when comparing calculated flows with real world experimentation, in particular to accommodate for flows shortly before and after purging, for example, or for flow above 15 ml/minute. Additionally based upon empirical observations, when the pump is filled with air, a mathematical constant is incorporated into the volume calculations. A determination that the pump is filled with air can be made by observing how hard the motor has to work, and knowing that the motor has to work harder to create vacuum changes when the system is filled with air as opposed to when the system is fluid filled.

When calculating milk volume pumped from the system 10, as stated, there is a need to distinguish between any air pumped by the system versus milk pumped from the system, as well as pumping mixtures of milk and air. When initiating a milk pumping/extraction session, there is air in the tubing 32 this initial volume of air needs to be pumped into the milk collection container 60 to prime the pumping system 10. Again, distinction between pumping air versus pumping milk can be recognized by correlating pressure changes with the amount of movement of compression member 38 needed to establish the pressure changes. For example, when air is in the tubing, a greater change in position, or more overall travel of the compression member 38 is needed to establish the same pressure change than that needed when the tubing 32 is filled with milk. Thus, relatively more motion of the compression member with relatively less pressure change indicates air in the tubing 32. This difference in pressure may also be detected when the compression member 36 is open (i.e., not closing off tube portion 32S) and compression member 38 is retracting and this increasing the vacuum pressure.

When a user has completed the pumping phase of extracting milk from a breast, it is useful and efficient to purge as much milk that remains in the tubing 32 from the tubing 32 and into the milk collection container 60. Ending of the extraction phase can be performed upon elapse of a predetermined extraction phase time, calculation of a predetermined amount of milk having been pumped, manual cessation of the extraction phase by the operator, or some other predetermined value having been achieved after performing the extraction. The direction of the pumping stroke of compression member 38 is reversed and the compression member 38 is run in the reverse direction to decrease suction within the tubing 32 and optionally create a small positive pressure within the tubing 32 to facilitate removal of the system 10 from the breast. Alternatively, the suction may be decreased to a level where a slight suction remains so that the user still pulls the system 10 of the breast to detach it. Preferably the vacuum is reduced to 0 mmHg, or a slightly positive pressure to automatically detach the system 10 from the breast. The end pressure value where the pressure reduction by reverse pumping is ceased can be in the range of about −20 mmHG (weak vacuum) to a positive 50 mmHg (e.g., the crack pressure of the valve to the container). The compression member 36 does not close off the tubing portion 32S during this process, rather, tubing portion 32S remains open. Initiation of this reverse pumping may occur automatically or, alternatively, may be initiated by the user. This process continues until the seal of the system 10 to the breast is broken, which is detected by the controller via sensor 54. Once exposure of the tubing 32 to atmospheric pressure is detected, the stroke direction of pumping is again reversed thereby pumping the milk in tubing 32 under positive pressure and driving the milk from the tubing 32 into the container 60. If by chance, the system 10 accidentally or otherwise becomes resealed to the breast during purge pumping, the system 10 can automatically shut down as it senses vacuum pressure being regenerated in the vicinity of the flange or breast/skin contact member 14.

The system 10 can be configured to distinguish whether it has been attached to the left breast or the right breast of the user. This can be useful for tracking milk volume output per breast, per session, total daily volume per breast, etc. When using two of the pump systems, the tracking of data for each breast can still be maintained accurately, even when one of the pump systems 10 is attached to the left breast during a current pumping session after having been attached to the right breast during a previous pumping session. In one embodiment, the pumping systems 10 can establish current location (i.e., left or right breast) by receiving a signal from the other pumping system having been attached to the other breast. This established relative left-right locations of the two pumping systems 10, so that each system 10 can accurately record as to whether milk is being extracted from the right breast or left breast. This identification is automatic, without any user input required and it also relieves the burden on the user to otherwise keep track of which pump system 10 is placed on each breast and to maintain this order with each successive pumping session. Left and right pump labeling is also contemplated such as by placing markings on the system housing or cover jack, for example, near the power connector.

Various approaches to assessing milk volume can be included in the pump system. Certain approaches are describe in co-pending International Application No. PCT/US15/50340, the entirety of contents of which are incorporated herein by reference. A further approach to assessing expressed milk volume involves placing one or more disposable data collection devices on the mom or child. One specific approach involves creating a boundary on the skin of a breast and employing a fiducial to conveniently measure the change in size of the boundary. This change in size is then correlated to milk production to arrive at a volume of milk expressed or pumped. A crib or bassinet can also include sensors and communication hardware that communicate with the pump system so both assess and management milk consumption and needs, and baby health.

The system 10 can calculate the pressure during operation in any of the manners described above. The suction (pressure) level can be varied as desired, and by continuously or repeatedly measuring/calculating pressure, the feedback provided by sensor(s) 54 to controller 52 provides a control loop that can be used to adjust the compression member 38 position and/or speed to vary the suction pressure to a level desired, or maintain a desired suction pressure in real time. Thus, controller 52 can control the positions and speeds of compression members 36, 38 to achieve any vacuum pressure pumping profile desired, and provide automatic, real time adjustments to maintain a desired vacuum pressure within the system. Also contemplated is responding in real time to maintain flow. This can accomplished independent or in conjunction with monitoring and regulating pressure in real time.

The controller 52 tracks the position of the compression member 38 relative to the tubing 32L, such as by keeping track of the driver 46 position or shaft position (interconnecting linkage between driver 46 and compression member 38), and calculates (or looks up) pressure based upon data received from sensor 54. The system controller or firmware is programmed with or retains information relating values detected by system sensors with driver positions and speed and system pressure. Thus, changes in position and/or speed of the compression member 38 by controller 52 can be controlled by resulting changes in pressure calculated or looked up, relative to the pressure sought to be achieved. As stated above, by using machine learning or supervised learning regression techniques, the system 10 can be trained to interpret the motor positioning and tubing strain (as well as motor speed or pump settings), while compensating for noise and hysteresis, to arrive at a pressure/vacuum level. More specifically, a neural net system or other mathematical regression can be incorporated into system firmware so that sensor input can be translated to pressure/vacuum levels. Controller 52 can thus control compression member 36 in a similar manner, but control of member 36 is more focused on position control, as the compression member 36 needs to fully close off tube portion 32S when maintaining latch suction against the breast/nipple. However, the closing off is timed and performed at the determined latch pressure, which is known from the data received from sensor 54.

Turning now to FIGS. 22-28, various aspects of remote control and data collection approaches are presented. In at least one contemplated embodiment, the system 10 can be configured to communicate with a server, a remote computer, smartphone or other device such as through signal, such as by Wi-Fi, BLUETOOTH, BLUETOOTH Low Energy (BTLE), RFID, NFC or the like. In particular, one or more chips can be incorporated into the controller of the pumping system 10 (by hard wire and/or wirelessly, preferably wirelessly) and configured to be in communication with an external computer. The controller and/or external computer communicates with the sensor(s)/chip(s) which indicate(s) when the system is in use, and can track usage. By tracking the times of use and/or number of uses, or even pump cycle counts, for example, the controller, or external computer can alert the user when it is time to change components or to report on usage aspects. In this way, information such as the tracking of extraction date and time, volume extracted, etc. can be recorded and stored with regard to each milk collection container used with the system 10 to extract milk. Thus, the system 10 can register individual milk collection containers, so that the user can readily identify when milk in each container was collected, the volume in each container, etc. The breast pump system can record the volume of milk in any given container during a pumping session. The data recorded can be sent to an external computer and/or over the Internet, either automatically or manually. Thus, user data and trends can be collected, stored and analyzed as they relate to volume (from each breast and in total), as can be the number of sessions on several dimensions (per day, week or month). Data and analytics can thus be provided to a user concerning pumping sessions.

In one particular approach, at least the session start time, the session end time and total volume of milk extracted from the breast can be stored and tracked. Sessions can be defined as the commencement of latch and can continue up to and through pauses of up to 5 minutes, for example. Thus, a pause of over 5 minutes can be defined as the end of the previous session. A language protocol is generated so that there is a two-way communication between an external device or program and the breast pump. That is, both the pump and external device can create and understand and are responsive to specific messages. Further, live data and historical data can be treated differently, and their data streams maintained separately. Live updates are generated and stored at the pump and are available by the external device to retrieve (for example, up or down button activations or volume updates). Accordingly, such live data can be reflected on and update the screen of the external device. Historical data is stored inside the pump in a stream and the pump can communicate with this stream to extract or act upon the same. An internal pump memory such as a disc within a chip or other internal flash stores, communicates with the pump so that session data is written to an internal history log. At the end of a session, for example, the pump will write the session data to its internal history log and the external device will ask if there is any data and if the pump indicates that there is, then the external device will download this historical data to update its non-live view screens. The external device can also make this same query after an extended time and then download multiple session data, and the query also can be made during a session. In one particular embodiment, as much as 600 sessions of data can be stored.

In one or more embodiments, the system can additionally or further include structure configured to accomplish or functionality operating as an Active Pause Mode, that allows the system to maintain latch vacuum, while remaining (especially under no/low flow) virtually silent. Such a system stays much quieter than pump mode, but ensures the system does not fall off the breast. It can be employed by the user mom when she needs to interact with others and does not want them to hear the pump, or for some other reason where she might not be ready to remove the device but does not want active pumping either.

Figure 22:
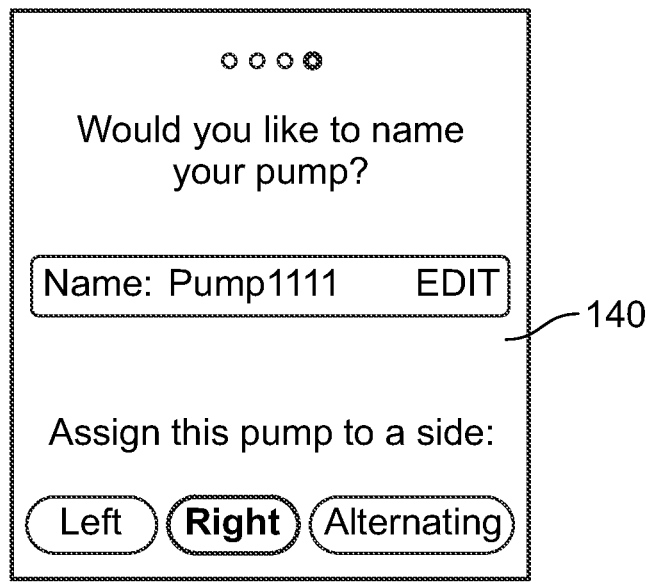
FIGS. 22-28 depict various aspects of a remote user interface system.
Figure 23:
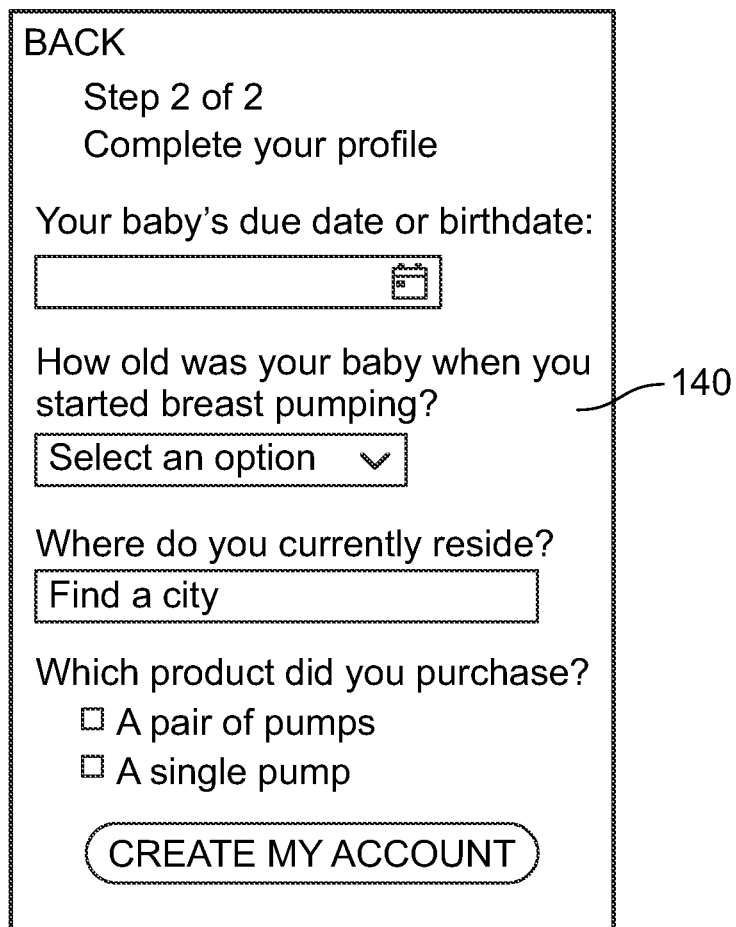
Figure 25:
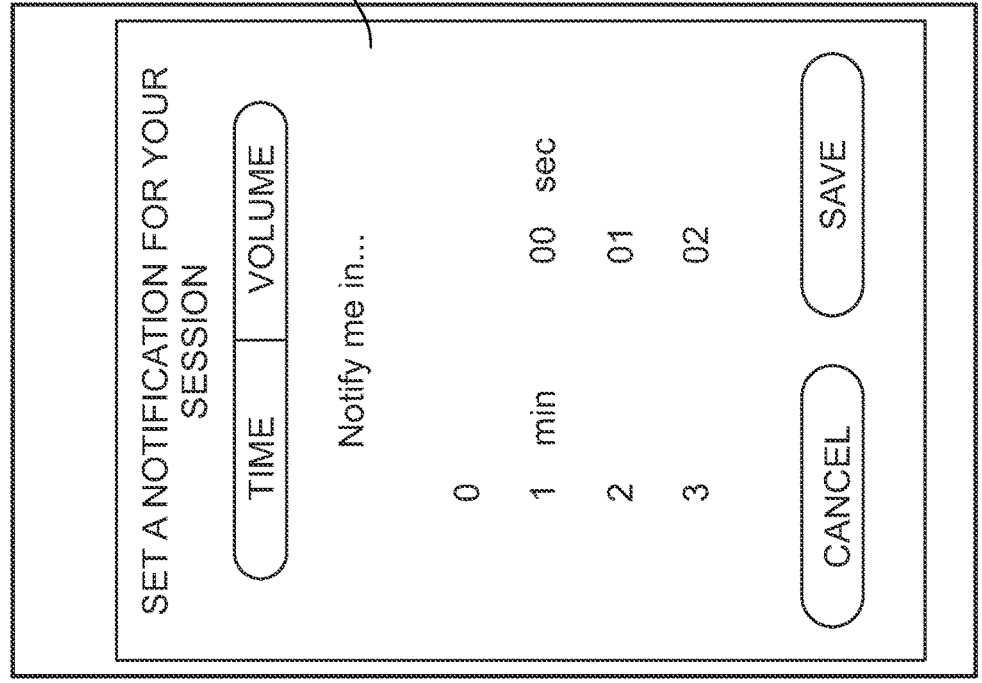
Figure 24:
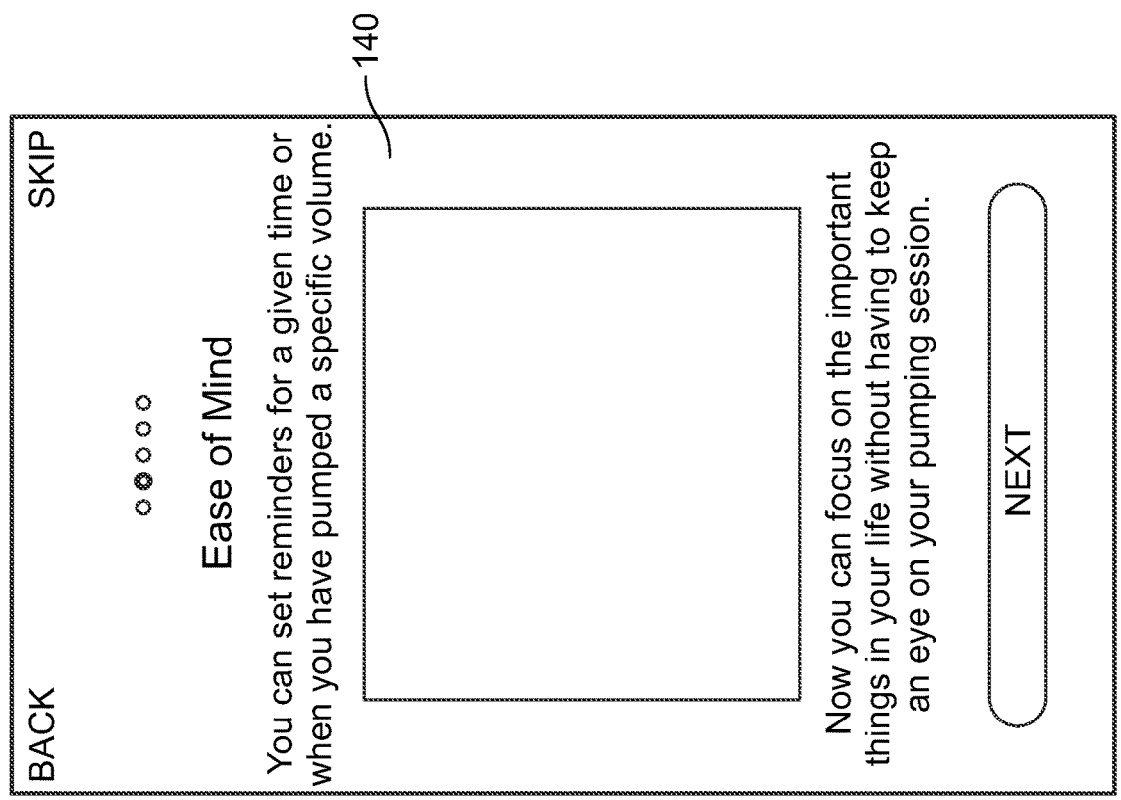
Figure 26:
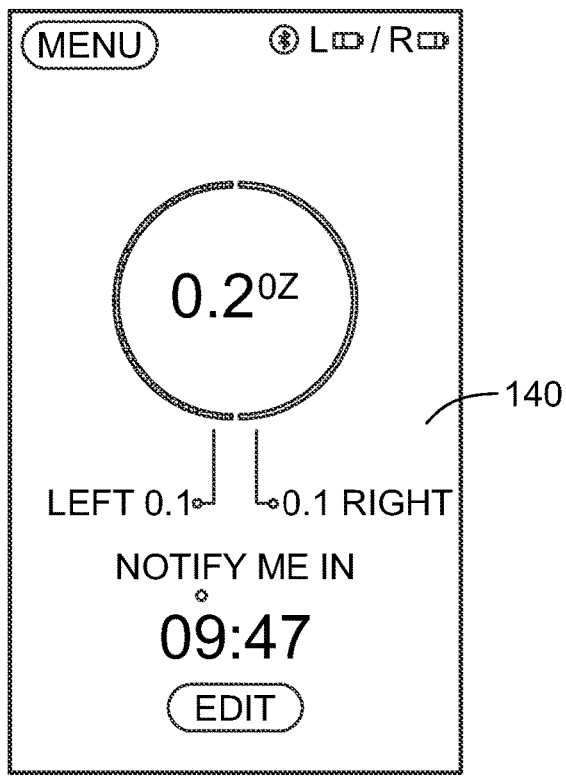
Figure 27:
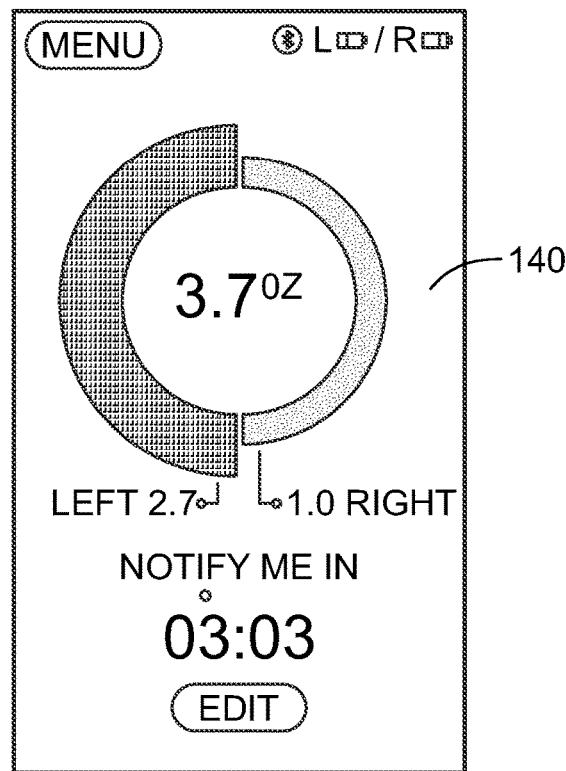
Figure 28:
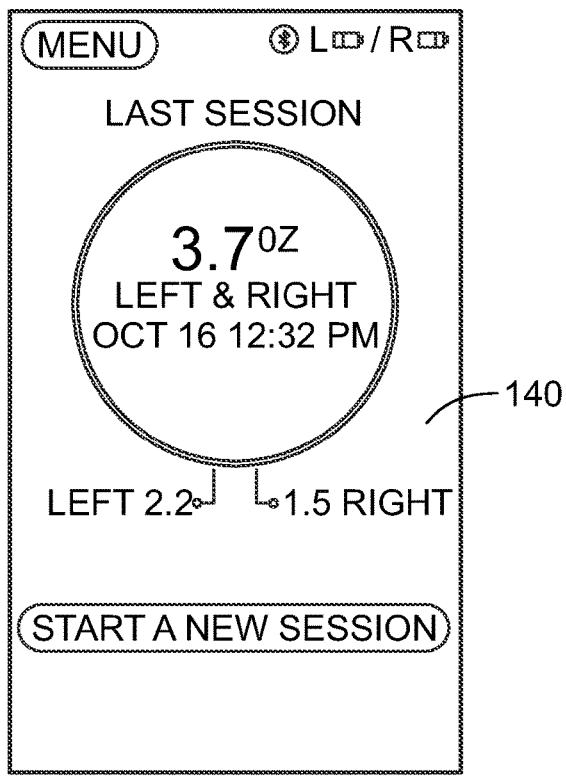

The remote user interface 140 on an external device can take a myriad of forms. The pump system can also be personalized such as by giving one or more pumps a name (FIG. 22). A user profile can be created for a child and linked to a child's birthdate (FIG. 23). Other details such as tracking the child's age when use of the system commenced can be gathered so that analytics pertinent to the child's age can be generated. In this way, pump performance can be tracked to the growth of the child. Reminders can be entered into the system (FIG. 24) so that the user can focus on matters other than breast pumping. Notifications can be keyed to time or volume of milk pumped while both of such criteria as well as battery life can be tracked and reflected on the remote computer (FIGS. 25-28). Easily understood and convenient graphics are contemplated for expressing status such as curved hemispherical strips 150 reflecting volumes pumped for each pump system, the same information also being shown in numerical form 152. Timing countdowns as well as information from one or more previous sessions can also be graphically displayed for effectively communicating with a user. The ability to remotely begin a new session can also be made available to the user.

Figure 29:
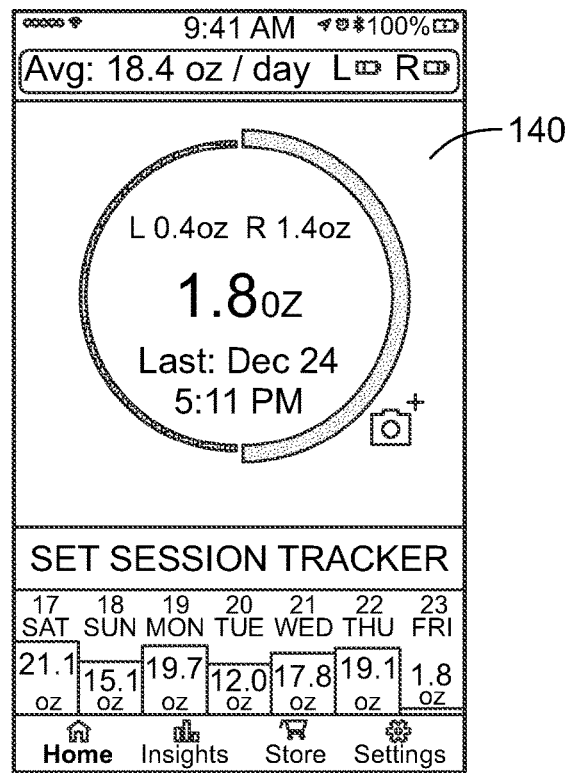
FIGS. 29-41 depict various further aspects of a remote user interface system.
Figure 30:
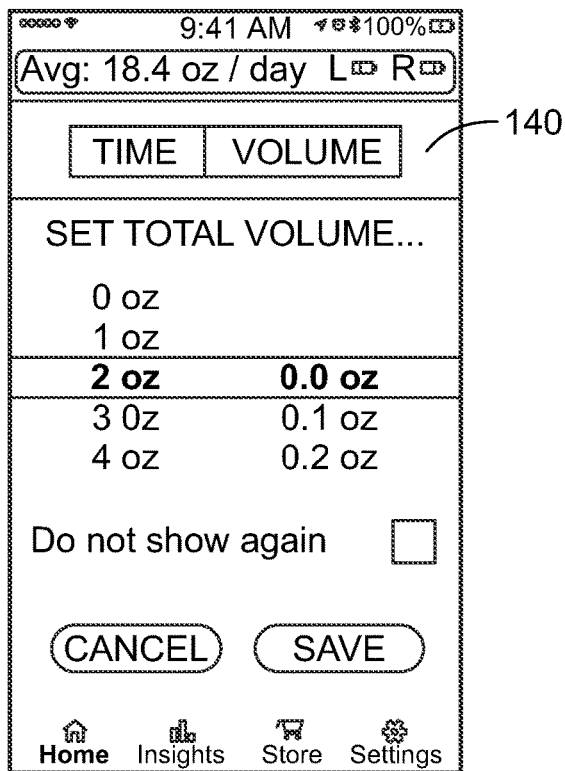
Figure 31:
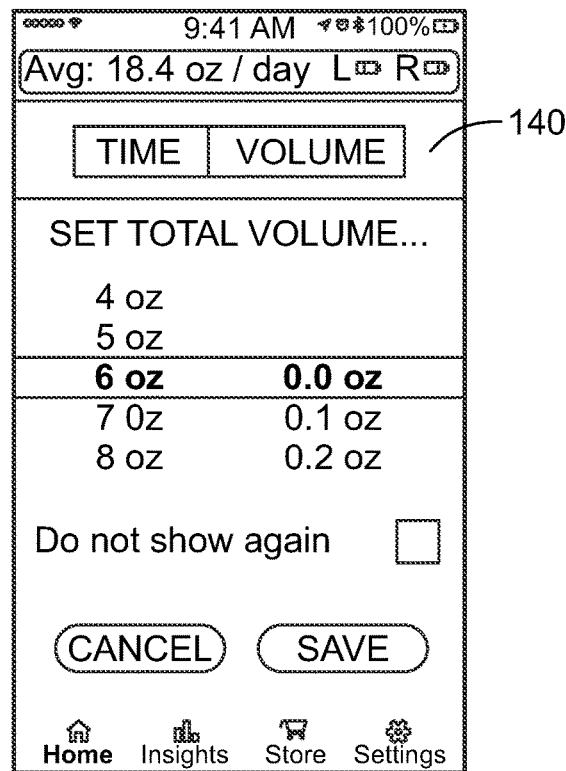
Figure 32:
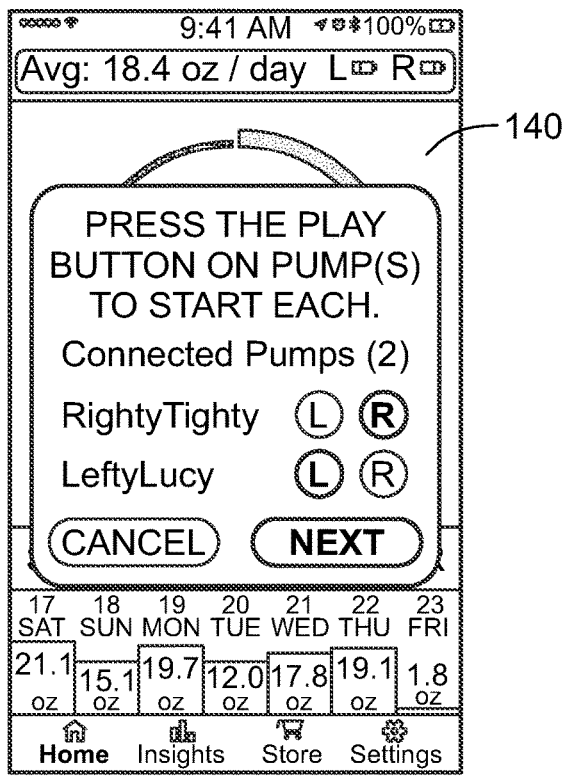
Figure 33:
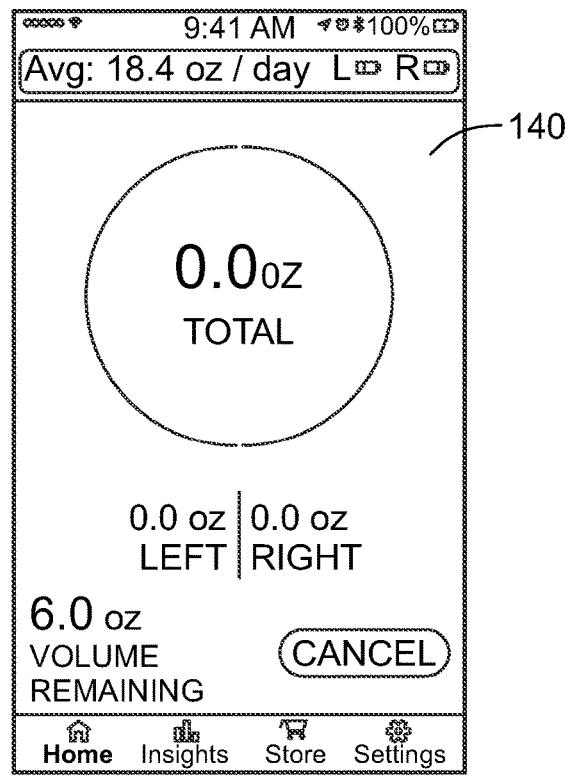
Figure 34:
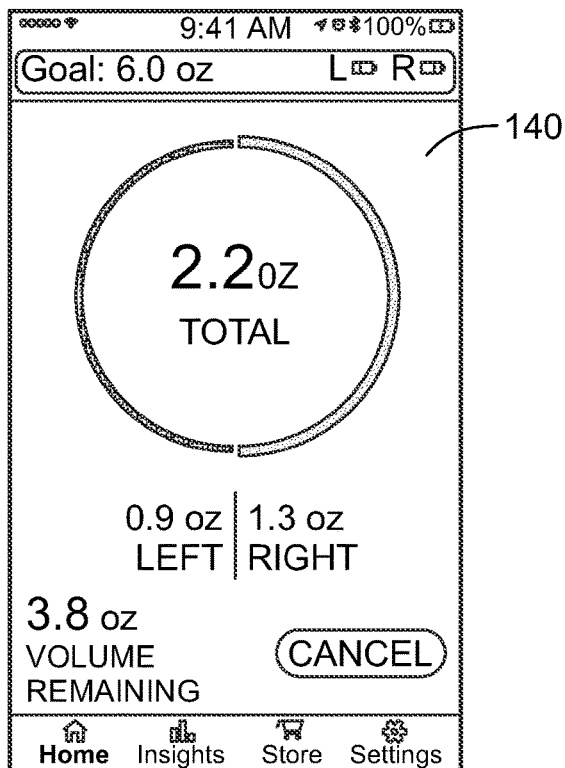
Figure 35:
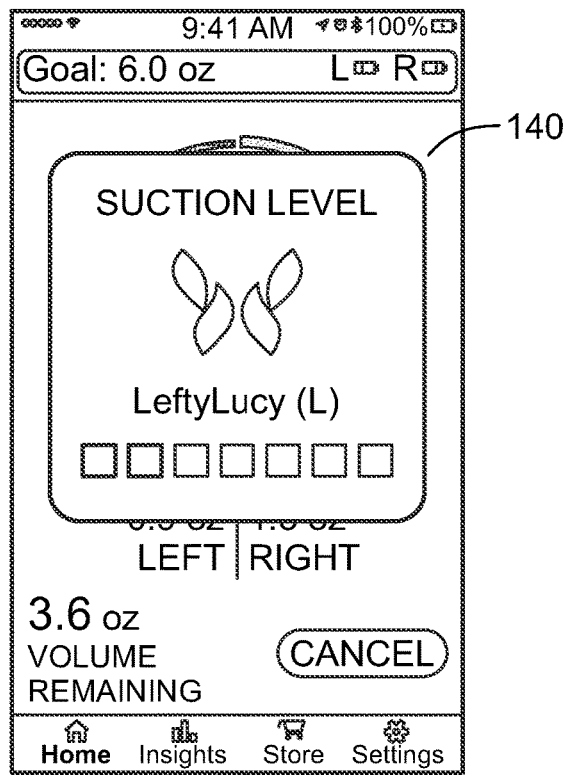
Figure 36:
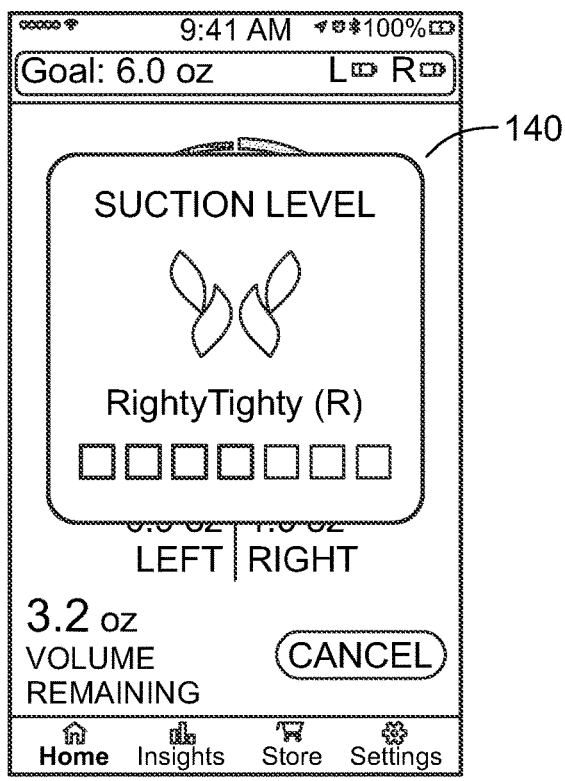
Figure 37:
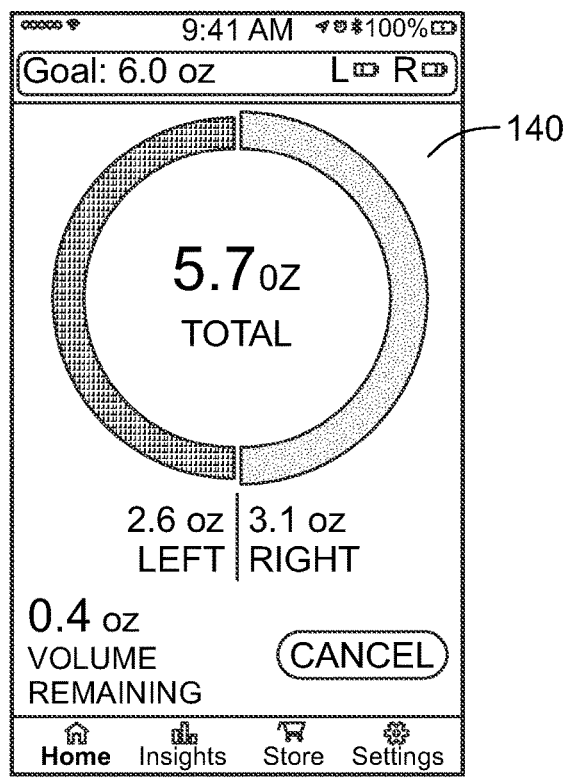
Figure 38:
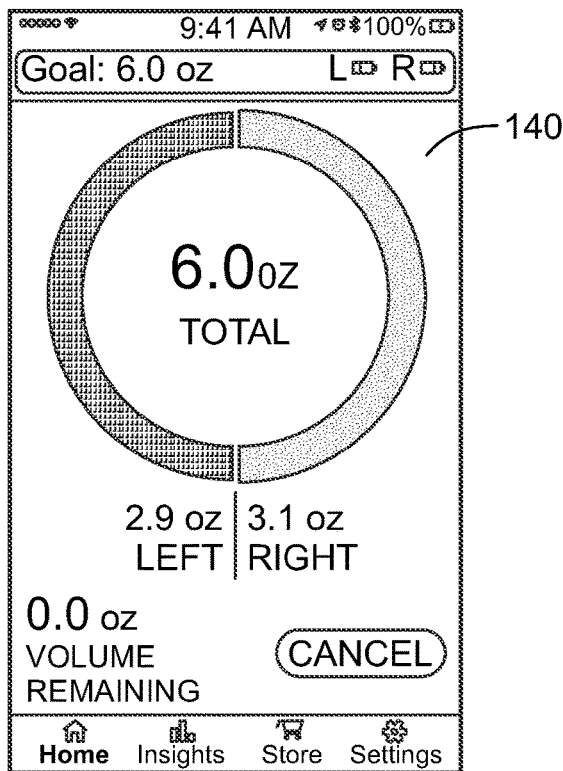
Figure 39:
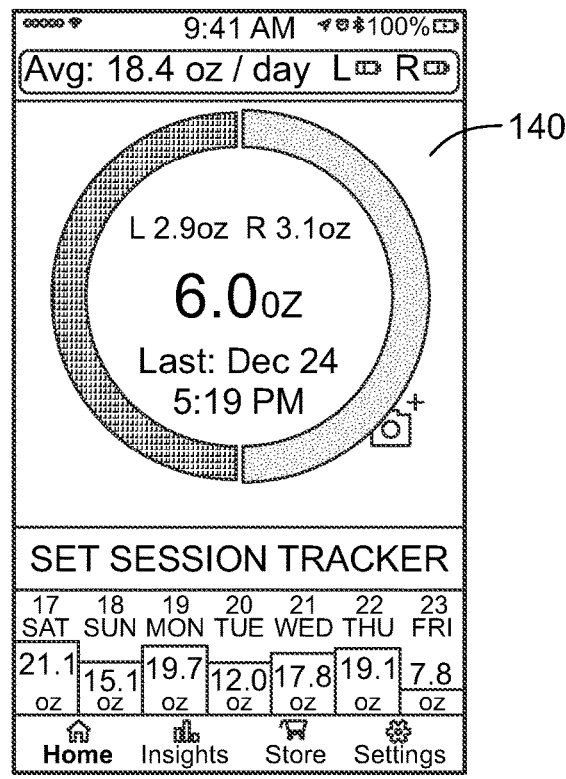
Figure 40:
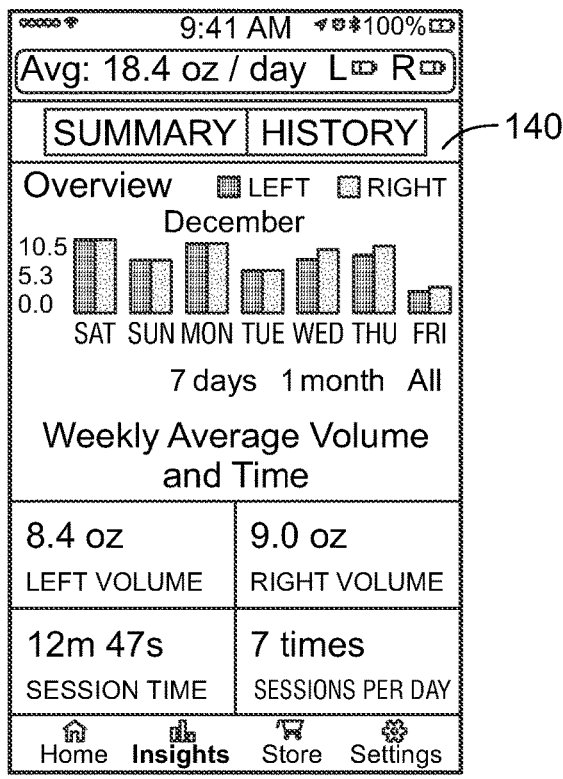
Figure 41:
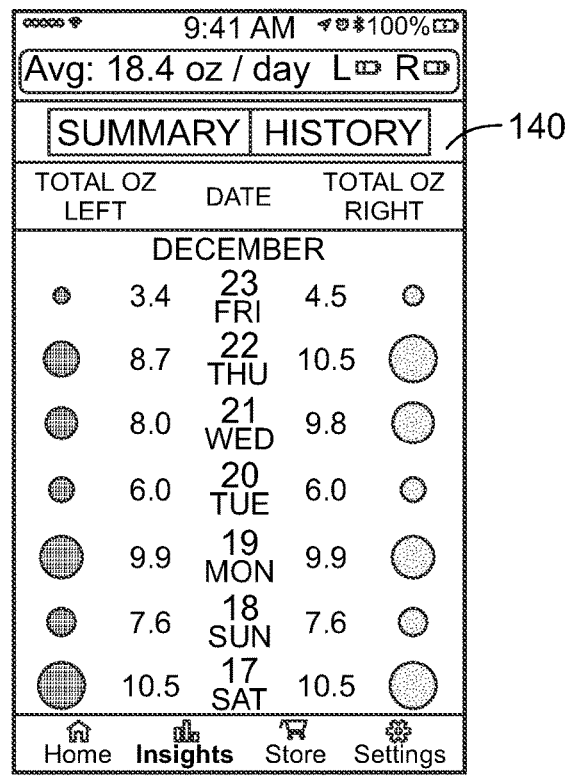

The remote user interface 140, whether provided as an App, on a cell phone, computer or other computing device, can also include specific user control functionality, and various related easy to understand displays (See FIGS. 29-41). As shown in FIG. 29, in one or more approaches, the amount of milk pumped is tracked by day, and an option is provided to the user to set a session tracker by day. The amounts pumped are also tracked by breast. A user can set one or more of time and volume of pumping by breast for one or more pumping sessions. For example (FIGS. 30-31), a volume target can be set by the user by various increments such as 0.1 ounces. This setting can be set and saved, or canceled. As shown in FIG. 32, the user can then control whether to pump with one or both breasts, and then the system starts tracking pumped volume (see FIG. 33). As pumping progresses (FIG. 34), easily readable curved bars reflect the amount of volume being pumped by each breast, the bars becoming thicker as more volume is pumped. The user can adjust suction levels for one or both of the pumps attached to a breast (FIGS. 35-36) to coordinate pumping or to otherwise pump as desired. After reflecting the changes in suction level, the user can return the system to tracking volumes pumped by breast (FIG. 37), and an indication of volume remaining to be pumped is also provided. Once the pumping target is met, such as a target volume (FIG. 38), the user interface will indicate that the session has been completed. Thereafter, an updated set tracker is presented, with an ability to set further pumping schedules (FIG. 39). The user can then select an option to depict a summary of pumping or a history of pumping (see FIGS. 40 and 41). The data provided by the user interface can include bar graphs and numerical data showing pumping by day and by breast and session times and number of session. Additionally, circles can be sized to represent relative amounts of pumping by date, and color coded by breast.

The pump system can also include a power management system that functions to save power. In one aspect, the pump system can be characterized as having multiple modules or threads, each running separate programs. Each thread, such as fifteen to twenty different threads, is designed to operate in a manner to save power. That is, each thread is controlled so that it seeks and finds its own maximum, minimum required power mode.

The pump system can be further configured so that the power management system includes a power hierarchy including various different levels at which the threads seek to achieve maximum, minimum required power. In one approach, the levels can include one or more of hibernate, standby, standby with LED's and active. Hibernate can be characterized as a deep sleep state and standby can be defined at a level where the system is running the computer chip and running calculations but not external components are being run. Standby with LED's can mean just that the LED's are engaged and active can mean that external components like the motors and sensors are working. The power system can thus function so that a query is sent to each thread asking for the thread's current state and it's minimum required mode. The power system then cycles through each thread and sets the power level at the maximum, minimum power level required so that each thread can properly operate.

In still yet further embodiments and approaches, the pump system can alternatively or additionally include built-in or computer or App based functionality to de-stress the user's life, empower the user to better take care of the nursing baby's health, maximize the user's mobility and freedom, and support all that is involved in becoming or being a parent. In these regards, pump system structure and functionality can include one or more of keying on pain points, physical conditions, sleep, pain relief, and post partum issues, tracking sleep, sensing and tracking baby vitals and movement, focusing on connected health with the mom as the caregiver, and/or providing education, guidance or instruction on movement and ways to carry a baby, fertility, post baby needs, health of the mom, ultrasound and fertility. The pump system can additionally include App integration with smart bottles, smart scales or the like to facilitate managing overall baby health and nutrition. App updates can additionally be provided about stimulation and letdown, and timing of pumping based upon such information, such as suggestion to begin pumping. System structure and functionality can also involve updating pumping profiles based upon baby age and needs, developing pumping functionality which enhance milk production, enhance efficiency or comfort or better mimic baby. Data can be stored in the cloud for analysis, and additional functionality can be provided to modify speeds and alternated between and among customized modes and profiles. Additional or a myriad of sizes of flanges and bag or container assemblies can be provided to the user as can nighttime pump functionality or programming including automated sessions with starts and stops.

Inventory management is further functionality that is provided as part of the structure of the pump system. In connection with the same, container assemblies can include structure that is scannable or which otherwise communicates with the inventory management system (eg., via bar codes, RFID chips). Further, operative communication structure can be provided so that the user can transmit data with and between a baby-center platform that stores data thus facilitating an avenue for the effective management of the baby's nutrition, and links can be made to automatically communicate with milk banks and donation centers. Additionally, a caregiver data share system can be included within the functionality and structure of the pump system. Texting is added to other forms and avenues for communicating such important and useful information.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure.

That which is claimed is:

1. A wearable, portable self-powered breast pump system sized and shaped to fit within a bra and configured for pumping milk from a breast, comprising:
    a breast adapter configured to contact and form a seal with the breast;
    a nipple receiving cavity connected to the breast adapter;
    a pumping mechanism including a motor fixed with respect to the nipple receiving cavity and configured to pump milk from the breast; and
    a milk collection container, the milk collection container configured to surround the nipple receiving cavity.

2. The system of claim 1, wherein the breast pump system automatically senses letdown.

3. The system of claim 1, wherein the breast pump system switches from letdown to extraction upon sensing a small volume of fluid has been collected.

4. The system of claim 1, further comprising a non-contact pressure sensor adjacent the nipple receiving cavity.

5. The system of claim 4, wherein the non-contact pressure sensor is used for controlling pumping cycles of the breast pump.

6. The system of claim 1, wherein the breast pump includes a letdown phase and an extraction phase.

7. The system of claim 6, wherein the extraction phase is for a predetermined amount of time.

8. The system of claim 1, wherein the motor is fixed above the nipple receiving cavity.

9. The system of claim 1, comprising two breast pumps, wherein each breast pump has left and right pump markings.

* * * * *